US010616219B2

(12) United States Patent
Stadnisky et al.

(10) Patent No.: US 10,616,219 B2
(45) Date of Patent: Apr. 7, 2020

(54) SINGLE CELL DATA MANAGEMENT AND ANALYSIS SYSTEMS AND METHODS

(71) Applicant: FlowJo, LLC, Ashland, OR (US)

(72) Inventors: Michael D. Stadnisky, Ashland, OR (US); Jay Almarode, Lebanon, OR (US)

(73) Assignee: FlowJo, LLC, Ashland, OR (US)

( * ) Notice: Subject to any disclaimer, the term of this patent is extended or adjusted under 35 U.S.C. 154(b) by 205 days.

(21) Appl. No.: 14/964,197

(22) Filed: Dec. 9, 2015

(65) Prior Publication Data
US 2016/0170980 A1 Jun. 16, 2016

Related U.S. Application Data

(60) Provisional application No. 62/090,589, filed on Dec. 11, 2014.

(51) Int. Cl.
| | |
|---|---|
| *H04L 29/08* | (2006.01) |
| *H04L 29/06* | (2006.01) |
| *G16H 10/40* | (2018.01) |
| *G16B 50/10* | (2019.01) |
| *G16B 50/20* | (2019.01) |

(52) U.S. Cl.
CPC .......... *H04L 63/0876* (2013.01); *G16B 50/10* (2019.02); *G16B 50/20* (2019.02); *G16H 10/40* (2018.01); *H04L 67/06* (2013.01); *H04L 67/12* (2013.01); *H04L 69/04* (2013.01)

(58) Field of Classification Search
CPC .......... G06F 17/3007; G06F 17/30138; G06F 17/30073; H04L 67/06; H04L 67/0876; H04L 63/0876; H04L 69/04; H04L 67/12; G16H 10/40

USPC .............................................................. 726/7
See application file for complete search history.

(56) References Cited

U.S. PATENT DOCUMENTS

| | | | |
|---|---|---|---|
| 4,845,653 | A | 7/1989 | Conrad et al. |
| 5,627,040 | A | 5/1997 | Bierre et al. |
| 5,739,000 | A | 4/1998 | Bierre et al. |
| 5,795,727 | A | 8/1998 | Bierre et al. |

(Continued)

FOREIGN PATENT DOCUMENTS

| | | |
|---|---|---|
| WO | 2013/143533 A1 | 10/2013 |
| WO | 2014022787 A1 | 2/2014 |

OTHER PUBLICATIONS

"Archival Cytometry Standard", International Society for Advancement of Cytometry Candidate Recommendation version 100929, Oct. 13, 2010; downloaded from http://flowcyt.sf.net/acs/latest.pdf.

(Continued)

*Primary Examiner* — Saleh Najjar
*Assistant Examiner* — Peiliang Pan
(74) *Attorney, Agent, or Firm* — Knobbe, Martens, Olson & Bear, LLP

(57) ABSTRACT

Disclosed herein are a number of example embodiments for data management and analysis in connection with life science operations such as flow cytometry. For example, disclosed herein are (1) a networked link between an acquisition computer and a computer performing analysis on the acquired data, (2) modular experiment templates that can be divided into individual components for future use in multiple experiments, and (3) an automated pipeline of experiment elements.

29 Claims, 18 Drawing Sheets

(56) References Cited

U.S. PATENT DOCUMENTS

| | | | |
|---|---|---|---|
| 5,962,238 A | 10/1999 | Sizto et al. | |
| 6,014,904 A | 1/2000 | Lock | |
| 6,221,592 B1* | 4/2001 | Schwartz | C12Q 1/6869 435/6.11 |
| 6,560,546 B1* | 5/2003 | Shenk | G01J 3/28 356/302 |
| 6,769,030 B1* | 7/2004 | Bournas | H04L 29/06 370/231 |
| 6,944,338 B2 | 9/2005 | Lock et al. | |
| 7,010,582 B1* | 3/2006 | Cheng | H04L 63/0815 709/219 |
| 7,194,531 B2* | 3/2007 | Donker | G06F 17/30887 707/E17.115 |
| 7,277,938 B2* | 10/2007 | Duimovich | H04L 41/5016 707/999.104 |
| 7,356,598 B1* | 4/2008 | Giroir | H04L 29/06 709/227 |
| 7,472,342 B2* | 12/2008 | Haut | G06F 21/604 715/234 |
| 8,835,358 B2 | 9/2014 | Fodor et al. | |
| 9,567,645 B2 | 2/2017 | Fan et al. | |
| 9,762,598 B1* | 9/2017 | Jagpal | H04L 63/1416 |
| 2003/0009470 A1 | 1/2003 | Leary | |
| 2003/0078703 A1 | 4/2003 | Potts et al. | |
| 2003/0088657 A1* | 5/2003 | Eggers | G16H 10/40 709/223 |
| 2004/0019690 A1* | 1/2004 | Cardno | H04L 29/06 709/230 |
| 2004/0061713 A1* | 4/2004 | Jennings | G06F 8/38 715/700 |
| 2004/0161767 A1* | 8/2004 | Baldwin | C12Q 1/689 435/6.11 |
| 2004/0242216 A1* | 12/2004 | Boutsikakis | H04M 1/274516 455/418 |
| 2004/0250118 A1* | 12/2004 | Andreev | H04L 63/0815 726/8 |
| 2005/0038608 A1 | 2/2005 | Chandra et al. | |
| 2005/0239125 A1* | 10/2005 | Hodge | C12Q 1/6809 435/6.11 |
| 2005/0247114 A1* | 11/2005 | Kahn | G01N 33/18 73/53.01 |
| 2005/0272085 A1* | 12/2005 | Hodge | C12Q 1/6876 435/6.12 |
| 2006/0014192 A1* | 1/2006 | Hodge | C12Q 1/6823 435/6.14 |
| 2006/0063264 A1* | 3/2006 | Turner | B01L 3/5085 436/8 |
| 2006/0148063 A1* | 7/2006 | Fauzzi | G01N 1/31 435/286.4 |
| 2007/0014305 A1* | 1/2007 | Assad | H04L 67/06 370/447 |
| 2007/0031823 A1* | 2/2007 | Bentwich | C07K 14/005 435/5 |
| 2007/0041395 A1* | 2/2007 | Boucek | H04L 63/083 370/437 |
| 2007/0128633 A1* | 6/2007 | Zozulya | C12N 9/1205 435/6.14 |
| 2007/0219728 A1* | 9/2007 | Papageorgiou | G06T 11/206 702/23 |
| 2008/0097917 A1* | 4/2008 | Dicks | G06O 50/22 705/51 |
| 2008/0109175 A1* | 5/2008 | Michalak | C02F 1/008 702/50 |
| 2008/0212643 A1* | 9/2008 | McGahhey | G01K 1/024 374/152 |
| 2009/0070841 A1* | 3/2009 | Buga | H04L 67/12 725/116 |
| 2009/0192363 A1* | 7/2009 | Case | G06F 19/322 600/300 |
| 2009/0204557 A1 | 8/2009 | Zhang | |
| 2009/0246782 A1* | 10/2009 | Kelso | B01L 3/502761 435/6.16 |
| 2009/0307757 A1* | 12/2009 | Groten | H04L 29/06027 726/4 |
| 2010/0042351 A1 | 2/2010 | Covey et al. | |
| 2010/0043047 A1* | 2/2010 | Archer | H04L 63/1416 726/1 |
| 2010/0070459 A1 | 3/2010 | Zigon et al. | |
| 2010/0070904 A1 | 3/2010 | Zigon et al. | |
| 2010/0161561 A1 | 6/2010 | Moore et al. | |
| 2010/0254581 A1 | 10/2010 | Neeser et al. | |
| 2011/0066385 A1 | 3/2011 | Rajwa et al. | |
| 2011/0099497 A1* | 4/2011 | Fok | G06F 3/0486 715/769 |
| 2011/0191899 A1* | 8/2011 | Ainley | C12N 15/8201 800/278 |
| 2011/0282870 A1* | 11/2011 | Herzenberg | G01N 15/1429 707/723 |
| 2012/0029832 A1* | 2/2012 | Dodgson | B01L 3/50825 702/19 |
| 2012/0140641 A1* | 6/2012 | Reese | H04L 43/12 370/245 |
| 2012/0179779 A1* | 7/2012 | Awasthi | H04L 67/1097 709/217 |
| 2012/0214190 A1* | 8/2012 | Hou | G01N 33/56972 435/29 |
| 2012/0215481 A1 | 8/2012 | Covey et al. | |
| 2012/0239297 A1* | 9/2012 | Yokota | H04W 4/006 702/1 |
| 2012/0245889 A1 | 9/2012 | Zhu et al. | |
| 2013/0091135 A1* | 4/2013 | Yokoi | G06F 17/30707 707/737 |
| 2013/0117298 A1* | 5/2013 | Ray | G06F 17/30091 707/769 |
| 2013/0177933 A1* | 7/2013 | Malisauskas | G01N 33/48735 435/13 |
| 2013/0197894 A1* | 8/2013 | Sablinski | G16H 10/20 703/11 |
| 2013/0226813 A1* | 8/2013 | Voltz | G06Q 20/38215 705/67 |
| 2013/0289925 A1* | 10/2013 | Jiang | G06F 19/00 702/122 |
| 2014/0072189 A1 | 3/2014 | Jena et al. | |
| 2014/0154789 A1 | 6/2014 | Polwart et al. | |
| 2014/0164564 A1* | 6/2014 | Hoofnagle | H04L 67/2823 709/217 |
| 2014/0213468 A1 | 7/2014 | Ehrenkranz et al. | |
| 2014/0222866 A1* | 8/2014 | Joneja | G06F 17/30073 707/785 |
| 2015/0120883 A1* | 4/2015 | Gurtowski | H04L 65/60 709/219 |
| 2015/0295972 A1* | 10/2015 | Hagan | H04W 4/026 709/203 |
| 2015/0363563 A1* | 12/2015 | Hallwachs | G06F 19/321 705/3 |
| 2016/0122341 A1* | 5/2016 | Vakalopoulos | C07D 471/04 514/210.21 |
| 2016/0130574 A1 | 5/2016 | Sadekova et al. | |
| 2016/0170980 A1 | 6/2016 | Stadnisky et al. | |
| 2016/0243251 A1* | 8/2016 | Blainey | C07K 14/00 |
| 2016/0328249 A1 | 11/2016 | Simm et al. | |
| 2016/0337786 A1* | 11/2016 | Kafle | H04W 4/001 |
| 2016/0362408 A1* | 12/2016 | Vakalopoulos | C07D 471/04 |
| 2018/0010134 A1* | 1/2018 | Sharp | C12N 15/102 |
| 2018/0165414 A1 | 6/2018 | Almarode et al. | |
| 2018/0340890 A1 | 11/2018 | Roederer et al. | |

OTHER PUBLICATIONS

Amir, El-ad David et al. "viSNE enables visualization of high dimensional single-cell data and reveals phenotypic heterogeneity of leukemia." *Nature biotechnology* 31.6 (2013): 545-552.

Bauer et al. (eds.), Clinical Flow Cytometry: Principles and Applications, Williams & Wilkins (1993).

Hsiao et al. "Mapping cell populations in flow cytometry data for cross-sample comparision using the Friedman-Rafsky test statistic as a distance meaure: FCM Cross-Sample Comparision." Cytometry, Part A, vol. 89, No. 1, pp. 71-88, Aug. 14, 2015.

(56) References Cited

OTHER PUBLICATIONS

International Search Report for International Application No. PCT/US2017/065987 dated Feb. 23, 2018.
International Search Report for International Application No. PCT/US2018/034199 dated Jul. 26, 2018.
Jaroszeski et al. (eds.), Flow Cytometry Protocols, Methods in Molecular Biology No. 91, Humana Press (1998).
Landy et al. (eds.), Clinical Flow Cytometry, Annals of the New York Academy of Sciences vol. 677 (1993).
Macosko, Evan Z et al. "Highly parallel genome-wide expression profiling of individual cells using nanoliter droplets." *Cell* 161.5 (2015): 1202-1214.
Newell et. al. Cytometry by Time-of-Flight Shows Combinatorial Cytokine Expression and Virus-Specific Cell Niches within a Continuum of CD8+ T Cell Phenotypes Immunity, 2012.
Ormerod (ed.), Flow Cytometry: A Practical Approach, Oxford Univ. Press (1994).
Pawley (ed.), Handbook of Biological Confocal Microscopy, 2nd Edition, Plenum Press (1989).
R. E. Bellman; Rand Corporation (1957). Dynamic Programming. Princeton University Press. Republished: Richard Ernest Bellman (2003). Dynamic Programming. Courier Dover Publications. & Richard Ernest Bellman (1961). Adaptive Control Processes: a guided tour. Princeton University Press.].
Roederer et. al. The genetic architecture of the human immune system: a bioresource for autoimmunity and disease pathogenesis. Cell. Apr. 9, 2015;161(2):387-403. doi: 10.1016/j.cell.2015.02.046. Epub Mar. 12, 2015.
Roederer et al. "Frequency difference gating: A multivariate method for identifying subsets that differ between samples." Cytometry. vol. 45, No. 1, pp. 56-64, Aug. 24, 2001.
Roderer et al. "Probability binning comparison: a metric for quantitating multivariate distribution differences." Cytometry, vol. 45, No. 1, pp. 47-55, Aug. 24, 2001.
Shapiro, Howard. Practical Flow Cytometry, 4th ed., Wiley-Liss (2003).
Shekhar, Karthik et al. "Automatic classification of cellular expression by nonlinear stochastic embedding (ACCENSE)." *Proceedings of the National Academy of Sciences* 111.1 (2014): 202-207.
Supplementary European Search Report for Application No. EP 15 86 6701 dated Jun. 21, 2018.
Tirosh, Itay et al. "Dissecting the multicellular ecosystem of metastatic melanoma by single-cell RNA-seq." *Science* 352.6282 (2016): 189-196.
Van den Bulcke, T. et al. SynTReN: A Generator of Synthetic Gene Expression Data for Design and Analysis of Structure Learning Algorithms, BMC Bioinformatics, Jan. 26, 2006; vol. 7, No. 43; pp. 1-12.
Van der Maaten, Laurens, and Geoffrey Hinton. "Visualizing data using t-SNE." *Journal of Machine Learning Research* 9.2579-2605 (2008): 85.
Van Der Maaten, Laurens, Eric Postma, and Jaap Van den Herik. "Dimensionality reduction: a comparative." *J Mach Learn Res* 10 (2009): 66-71.
International Search Report and Written Opinion dated Jun. 16, 2016 in International No. PCT/US15/65045.

* cited by examiner

```xml
<?xml version="1.0" encoding="UTF8"?>
<Protocol templateName="PBMC.Populations.wspt" >
<Protocol templateName="Low.PBMC.Script.wspt" >
<Protocol templateName="Low.PBMC.Report.wspt" >
<Constraint groupName="Low PBMC" statistic="groupCount" eval=">0" />
</Protocol>
</Protocol>
<Constraint groupName="Experimental" statistic="groupCount" eval=">0" />
<Protocol templateName="PBMC.Bind.CD3Pos.wspt" />
<Protocol templateName="PBMC.Bind.CD19Pos.wspt" />
<Protocol templateName="PBMC.Bind.CD3Neg.CD19Neg.wspt" />
</Protocol>
</Protocol>
```

Figure 12

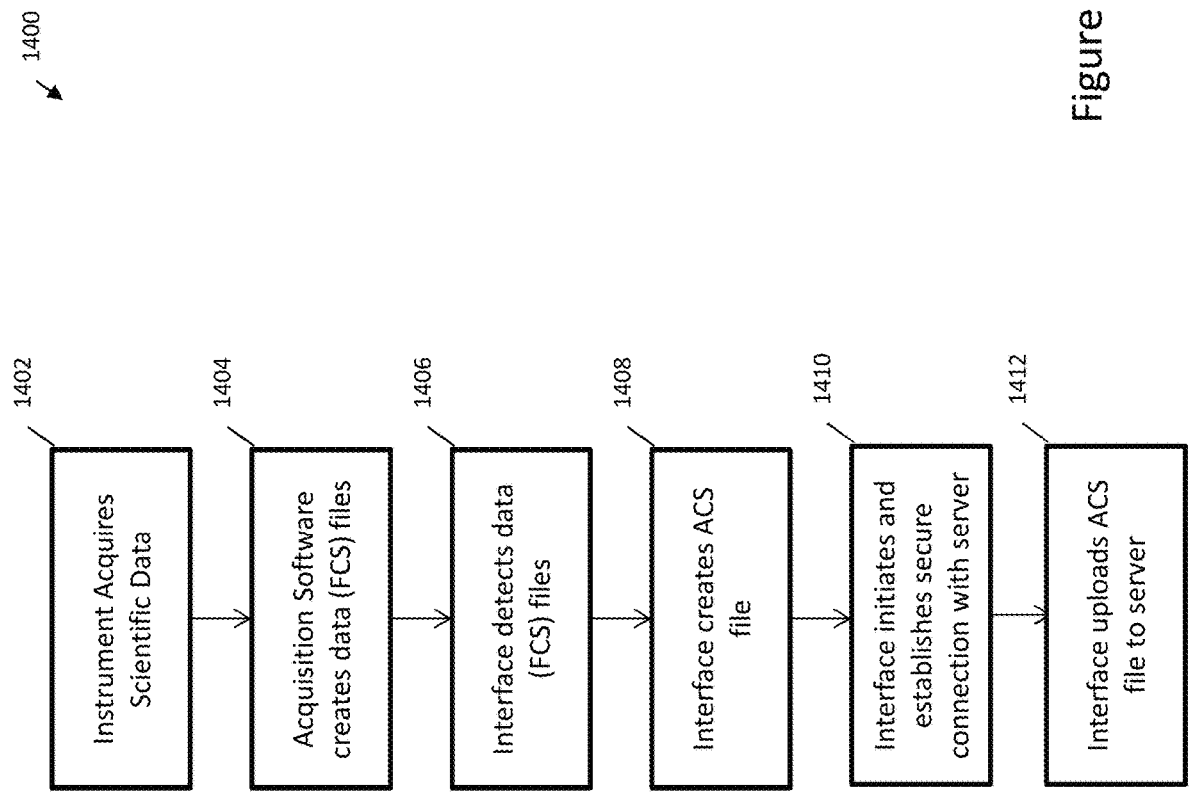

Figure 16

1) Annotation Keywords (aka Metdata): Patient, Cytometer, when sample was run, etc.

.fcs files

2) Listmode Data:

*Each cell = row of values*

Figure 17

SINGLE CELL DATA MANAGEMENT AND ANALYSIS SYSTEMS AND METHODS

CROSS-REFERENCE AND PRIORITY CLAIM TO RELATED PATENT APPLICATION

This patent application claims priority to U.S. provisional patent application Ser. No. 62/090,589, filed Dec. 11, 2014, the entire disclosure of which is incorporated herein by reference.

INTRODUCTION

Most single-cell analysis and sorting experiments run at a core facility far from where the data is analyzed, and data management is a key challenge for life scientists. Generally, a USB drive or other examples of "sneakerware" are typically used to transfer life science data from an acquisition instrument (or from an acquisition instrument-associated computer, which has software that controls the operation of the acquisition instrument) to another computer for a detailed analysis of the life science data. In other words, data gathered from an instrument, such as a flow cytometer, is manually transferred to another non-core or individual laboratory computer for archiving and analysis using analysis software. Therefore, a scientist must gather data at the instrument, transfer the gathered data to a mobile disk drive, such as an external hard drive or a flash "thumb drive", and physically bring the mobile disk drive to another computer, and finally copy the data from the mobile disk drive to the another computer where data analysis may be performed.

One of the reasons data must be manually transferred from an instrument-associated computer to a computer tasked with analyzing the data is because instrument-associated computers are frequently either (1) not connected to any network, or (2) if connected to a network the network is a site intranet and not the Internet. Furthermore, even for a computer that is connected to a network such as the Internet, no current solution exists that efficiently and automatically transfers data from an instrument-associated computer to a data analysis computer or another computer. Thus, a scientist or data manager must either manually move the data using a mobile disk drive or by "dragging and dropping" the acquired data to other computers. In either scenario, data quality is not checked in transit. However, data quality for acquired life science data is highly important because of the impact of such data on medical research and studies as well as individual health.

In addition to data transfer and quality, life science experiments are often repeated using many shared characteristics. However, with conventional experiment technologies, even though a second experiment may have many of the same settings and variables as a first experiment, life scientists are forced to perform numerous tasks redundantly while creating an experiment. Conventional methods to expedite an experiment include using a conventional experiment template. Conventional experiment templates are computer files which themselves contain instructions which direct the analysis of data, and they are conventionally stored on the computer at which analysis occurs, namely, the non-core or individual laboratory computer. Such templates depend on correct and consistent labeling of metadata, and thus at present they are used almost entirely in repeated experiments. Moreover, because such templates are stored on the non-core or individual laboratory computer, transfer is required before any data is analyzed. However, these conventional templates are of limited use when experiment parameters change. For example, if a researcher wanted to create a new experiment with only one parameter changed, such as changing the reagent used during acquisition, the researcher must create an entirely new template even though the experiment's analysis was almost entirely the same except for the changed reagent.

In addition, conventional templates needlessly over-consume processor and analyst bandwidth. A conventional experiment template contains all the sample organization, analysis, and reports within a single template. According to the method defined by conventional experiment templates, if 1000 samples were collected, the sample organization, analysis, and reporting steps defined by the conventional template would be performed on all 1000 samples. However, due to the nature of single-cell research, only a subset of the samples might be interesting to a researcher. As such, a computer performing analysis or a scientist performing manual clustering would perform analysis, reporting, gating, etc. on all 1000 samples, even though some analysis steps are unnecessary.

Repeated experiments also cause a manual analysis bottleneck, especially due to the significant increase in throughput by modern single cell acquisition technology. Researchers whose experiments change frequently in design bear the burden of repetition during data pre-processing, clustering of common experimental elements, and post-processing. However, of the three repeated phases, the most time-consuming is the manual clustering step ("gating"). The first few steps of manual clustering e.g. on single cells, live cells, and lymphocytes are very frequently shared between many (if not all) experiments. There are many common elements in the gating or manual clustering for several experiments as experiments must be repeated, and frequently, a base set of reagents (and thus gates) is used to define a cell population, while markers of interest on top of that base are the only variable that changes. Thus, for each experiment, a researcher generally performs the same or similar manual clustering for each experiment, thereby causing a manual analysis bottleneck. This manual analysis bottleneck is highlighted by the number of commercially available reagent panels that allow a user to phenotype common lymphocyte subsets, and so gating on cell types will be essentially the same every time this panel is used.

Due to the manual analysis bottleneck and the lack of automation of multiple similar experiments on a data set, there exists a need in the art to perform single cell and life science experiments more efficiently.

It is in view of the above problems that inventive embodiments described herein were developed to provide technological solutions that improve how life science experimental data can be collected and analyzed.

According to an example embodiment, disclosed herein is a networked link between an acquisition computer and a computer performing analysis on the acquired data. In an example embodiment, this link can be designed as an intelligent bi-directional electronic link that not only permits scientific data to be efficiently transferred from a scientific instrument and associated computer to a remote computer system capable of performed advanced analytics on such data but also permits the remote computer system to control the operations of the scientific instrument. Such a link can be created by an interface that resides on an acquisition computer associated with a scientific instrument. Thus, according to an example embodiment, scientific data can be transferred, optionally in real-time, to a remote server for analysis. In another example embodiment, operational data can be passed to/from the scientific instrument via the interface. The bidirectional passing of information can include, e.g., the instrument parameters like optical filters, voltages, and type of physical storage of samples (tubes, different sizes of plates).

Additionally, data files from acquisition instruments are typically written to disk (and frequently stored in a local database.) Due to the limited local storage capacity and database performance limitations when running on a workstation, the conventional workflow requires frequent manual deletion of raw data, without any confirmation that said data has been transferred faithfully and/or archived by a life scientist on another storage device or location. Thus, confirmation and notification of successful data transfer (and possible downstream analysis) is very helpful in ongoing data management and ensuring that a copy of the raw data is available and backed up, not stored on the acquisition-associated computer.

According to another example embodiment, disclosed herein are modular experiment templates that can be divided into individual components for future use in multiple experiments.

According to another example embodiment, disclosed herein is an automated pipeline of experiment elements.

The modular experiment templates provide easily reusable template components that can quickly change a single experiment parameter or be replaced with a different template component to save time in creating experiments and analysis results. These modular templates not only find data interesting to a researcher or scientist, but they may also generate batch reports or reports for various populations.

Further, the automated pipeline may tie the created modular template components together for automated experimental analyses.

The automated pipeline may also shorten the time period between acquisition, analysis, and reporting of data to near zero. Thus, set-up and execution occur significantly quicker than the conventional technology.

Further features and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings:

FIG. 12 illustrates sample XML code for a protocol pipeline.

FIG. 14 illustrates a method 1400 for uploading scientific data to a remote server.

FIG. 16 illustrates an example protocol pipeline XML document.

FIG. 17 illustrates an example ACS file format.

DETAILED DESCRIPTION OF EXAMPLE EMBODIMENTS

Figure 1:
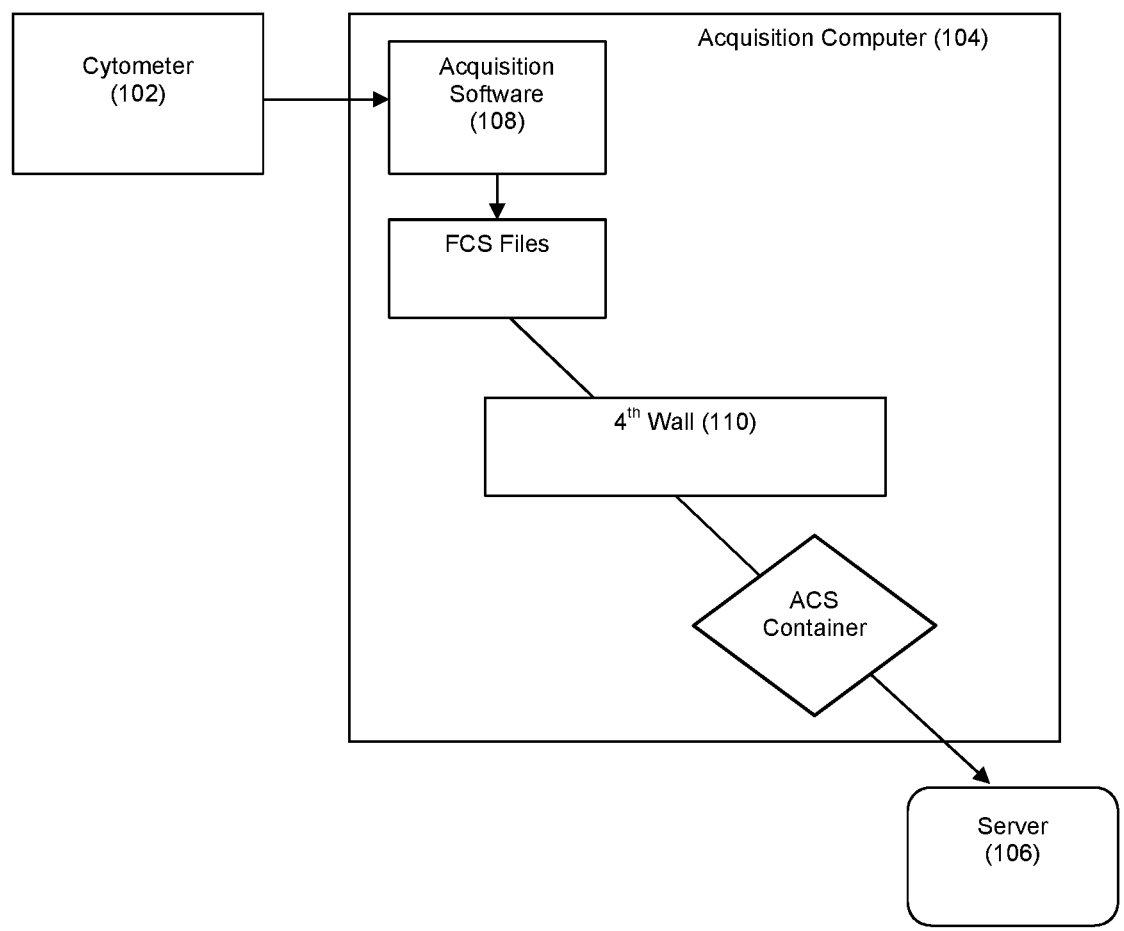
FIG. 1 illustrates a system diagram for an example embodiment.

Referring to the accompanying drawings in which like reference numbers indicate like elements, FIG. 1 illustrates a system diagram. As shown in FIG. 1, a data acquisition instrument 102 is connected to an acquisition computer 104. In the example embodiment shown in FIG. 1, the acquisition instrument 102 is a flow cytometer. However, it should be understood that instruments other than flow cytometers may be used as the acquisition instrument 102, such as mass cytometers, microarrays, genotyping and sequencing instruments, cell sorters, mass cytometers, digital droplet and real-time polymerase chain reaction instruments, etc. However, for the purpose of explanation, a flow cytometer will be used as an example embodiment herein as the inventors believe that the technologies described herein are particularly innovative and useful with regard to flow cytometry.

The acquisition computer 104 is connected to a server 106 through a network connection, such as over the Internet, over a subnet, over an intranet, or through the Internet to a cloud.

The acquisition computer 104 executes acquisition software 108, and the acquisition software 108 is capable of adjusting one or more parameters (e.g. voltage, flow rate, etc.) of the acquisition instrument 102 for a sample being tested. Such acquisition software 108 may also display initial sample information while acquiring sample data to provide feedback for a user to assess whether the parameters are correctly set. The acquisition software 108 may vary depending on the manufacturer of the acquisition instrument 102.

The acquisition software 108 receives data signals from the acquisition instrument 102 indicating results of a sample being analyzed by the acquisition instrument 102. For example, when the acquisition instrument 102 is a flow cytometer, the data generated by the acquisition software 108 may indicate any or all of the number of cells in a sample; metadata including the instrument type, operator and time of collection, etc.; event-level columnar data with fluorescence values for each individual event (which in this case is an individual cell). The results of data acquisition and sample analysis may be contained within one or more flow cytometry standard format files (e.g., a FCS file). The acquisition computer 104 creates one or more FCS files based on the signals and data provided by the acquisition instrument 102. However, it should be understood that other file formats may be used, particularly if the acquisition instrument 102 is not a flow cytometer. The acquisition software 108 may further generate metadata about the sample that indicates things such as acquisition instrument ID, patient ID, acquisition conditions and parameters, etc.

The acquisition computer 104 also includes an interface 110 that permits the acquisition computer 104 to automatically transfer acquired sample data to another computer (e.g., an interface 110 to a server 106). FIG. 1 depicts this interface 110 by way of example as the "4$^{th}$ Wall". As an example of the other computer to which the acquired data is transferred, the server 106 may be a remote server 106 dedicated to flow cytometry analysis. In the remote server 106 embodiment, the acquisition computer 104 may access the server 106 over a network. The interface 110 to the server 106 provides a data transfer link and a method for data analysis automation, which will be described in more detail below.

The interface 110 may be embodied as processor-executable program instructions that are resident on a non-transitory computer-readable storage medium such as computer memory. In an example embodiment, the interface 110 is resident on the acquisition computer 104. However, it should be understood that the acquisition computer, in some instances, may be part of the scientific instrument 102 itself, in which case the interface 110 would be resident on the scientific instrument 102. The interface 110 could also be resident on a small USB hardware-computing device that can be connected to the scientific instrument 102 and/or acquisition computer 104. In an example embodiment, acquisition software may call the interface 110, e.g. to push data immediately following an acquisition run or to push data real-time to server 106. In an example embodiment where the interface 110 supports bidirectional communication, the interface 110 may be used to setup the configuration of the instrument 102 which can be set by the acquisition software, and may be used during instrument operation to pass notifications and operational status data in the manner described herein.

The interface 110 may package the FCS files generated by the acquisition software 108 in a file container. While the file container may exhibit any of a number of file formats, the exemplary embodiments use a file format that is similar to a zip file format called an archival cytometry standard (ACS) file, discussed in greater detail below.

The server 106 comprises a processor and memory as well as data storage, such as a database. Processor-executable instructions resident on a non-transitory computer-readable storage medium (such as memory) may be executed by the processor to perform tasks described herein. The acquisition computer 104 may similarly comprise a processor and a memory, and where processor-executable instructions resident on a non-transitory computer-readable storage medium (such as memory of the acquisition computer 104) may be executed by the processor of the acquisition computer 104 to perform tasks described herein for the acquisition computer 104.

The description that follows will elaborate on a number of different aspects of the inventive technology described herein, including but not limited to (1) an interface 110 between an acquisition computer 104 and a computer performing analysis on the acquired data, (2) modular experiment templates that can be divided into individual components for future use in multiple experiments, and (3) an automated pipeline of experiment elements.

Figure 2:
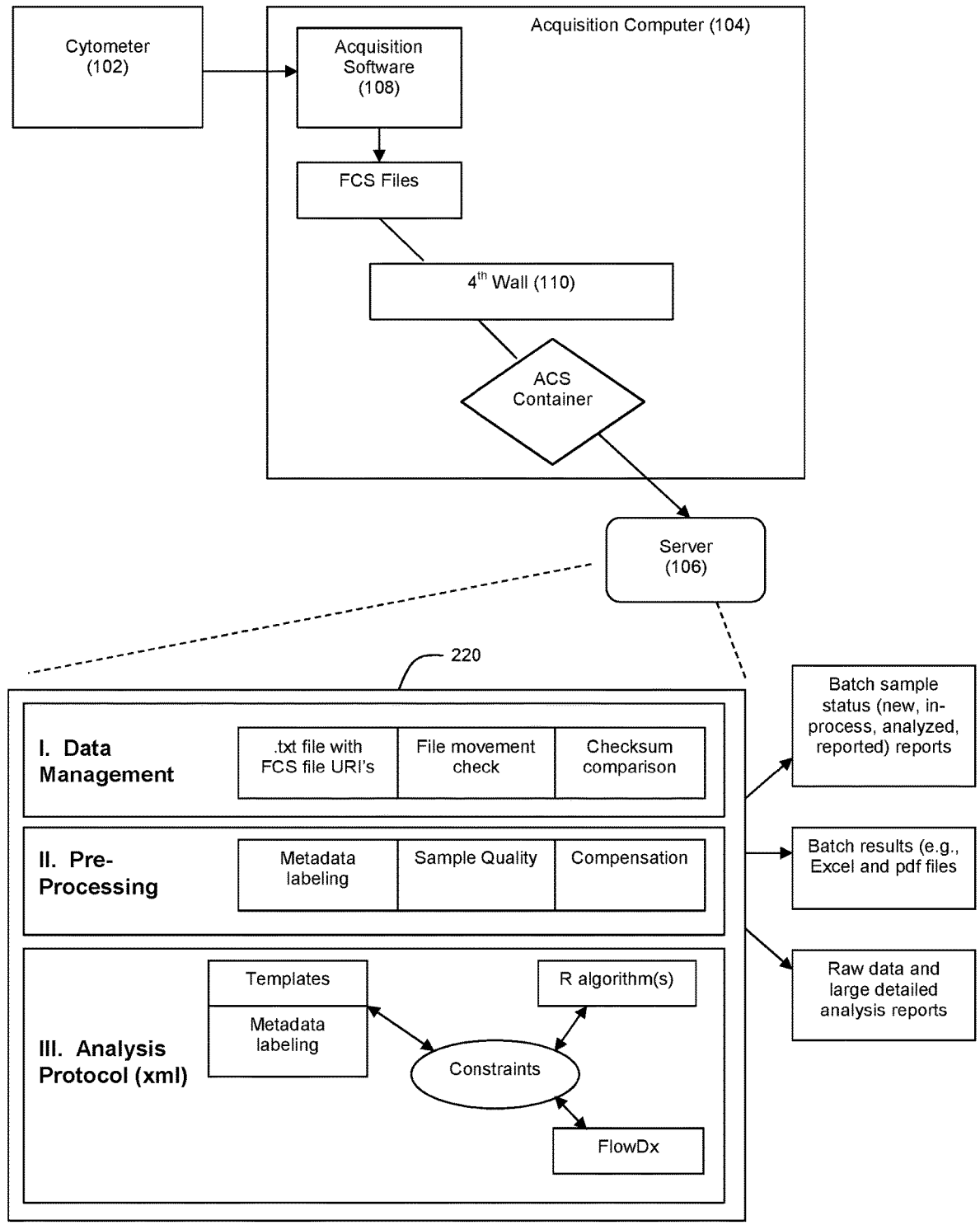
FIG. 2 illustrates an expanded view of a server illustrated in FIG. 1.

Interface Between an Acquisition Computer and a Computer Performing Analysis on the Acquired Data FIG. 2 illustrates an expanded version of FIG. 1 to illustrate some of the functions of the interface 110 (labeled as 4$^{th}$ Wall in FIG. 1) and functions for the server 106.

As the acquisition instrument 102 generates data, the acquisition software 108 creates files containing the data acquired by the acquisition instrument 102. FIG. 2 illustrates an FCS file as being the file type containing information about the samples analyzed by the instrument 102, but the files may also be PDF files, XLS files, CSV files, or any other file type suitable for storing acquisition data.

The interface 110 may take the form of another software module executed by a processor of the acquisition computer 104. Interface 110 may interact with its host in any of a number of modes of operation—such as a user-triggered mode, an automated data push mode, and an on-demand service call mode.

In an example embodiment for a user-triggered mode, the interface 110 can be configured to execute in response to user input. In such a case, a user may provide input that causes the interface 110 to execute after the user has operated the scientific instrument 102 to analyze a sample.

In an example embodiment for an automated data push mode, the interface 110 can be configured to perform an automated data push to the server 106 by executing as a script that constantly runs in the background of acquisition computer 104 or is triggered to run at various times (e.g., time-based or schedule-based triggering). With such an embodiment, a user configures the interface 110 to search a specified file directory for FCS files to be analyzed, which may be called a "watch folder" (see, for example, FIG. 13A discussed below). The interface 110 can then automatically monitor the watch folder for new data files (such as FCS files). Upon detection of a new data file in the watch folder, the interface can operate to transfer the new data file to the server 106.

In an example embodiment of an on-demand service call mode, the interface 110 can be configured to be invoked as a service by a call from another software application such as acquisition software 108. In such an embodiment, the interface 110 operates in conjunction with the acquisition software 108 or is a module contained within the acquisition software 108. The acquisition software 108 can be configured to send a notification to the interface 110 when it creates a new data file such as an FCS file. This notification can identify the location within a file directory where FCS files are located, and the interface 110 can then automatically upload the FCS files to the server 106 at the direction of the acquisition software 108. These notifications with file location identifications can be passed to the interface 110 through a command line invocation of the interface by the software module 108. The notification may further indicate when the data acquisition for a given FCS file has been completed so that the interface is able to send a completed FCS file.

In yet another example embodiment, the interface 110 may periodically upload data to the server 106. For example, in an automated push mode embodiment, the interface 110 may query known locations where FCS files are stored to determine if any new FCS files have been created or any previously known FCS files have been modified since the time of the previous upload. If the interface 110 determines that a new file has been created (or a file is newly modified), and is not in the process of being created (such as by searching for temporary files), the interface 110 will create a file container and upload the data via the file container. In either embodiment, the interface 110 targets the file directory location of one or more FCS files and creates a new container file containing all the relevant FCS files. For example, the file created by the interface 110 may be an ACS file or a Zip file. The ACS file may include all the FCS files generated by the acquisition software 108 based on the findings of the acquisition instrument 102 for a given sample. The ACS file may further include associated artifacts from an experiment conducted by the acquisition instrument 102.

The ACS file format includes data and metadata describing the subject being analyzed as well as acquisition conditions (see, for example, FIG. 17 which shows an example ACS file format where the file includes listmode data that represents the scientific data itself as well as metadata). The ACS file bundles the data derived from an experimental sample with different components describing cytometry experiments. The ACS container has both the raw data and any associated files compressed together, and metadata may be written into the raw data files (as a header) or associated by sample name, sample location (Well A2 should have this metadata), or other lookup criteria set by the user. Examples of associated files may include screenshots of analysis performed on the acquisition computer, tabular metadata or data associated with the samples, or a form that must be associated with the samples per the processing requirements of the clinical laboratory SOP.

The ACS file may further include a manifest that lists all the FCS files contained within the ACS file. To do so, the interface creates an index of files which is the list of files and folders, analogous to a file directory listing. The manifest may also include checksum values, the laboratory the data is associated with, and how it should be analyzed. The latter two can be set by a user through the interface application.

The ACS file may also capture relations among data contained in FCS files and the associated metadata and other components The ACS file may do this using any of the filename or metadata which is in the header of the files to either associate data together i.e. by samples which have been treated the same way. In addition, it may use other tabular data which indicates the relationships between raw data files via a 'lookup' as described, above, and the ACS file also includes support for audit trails, versioning and digital signatures. Though the manifest, the individual who ran the experiment, the user who uploaded the data, the timestamp, and any versioning may be supported. In addition, the compressed file archive may be digitally signed before upload. The ACS container is based on the ZIP file format with an XML-based Table of Contents specifying relations among files in the container.

When the interface 110 creates the ACS file, the interface 110 packages all FCS files acquired from a sample by the acquisition instrument 102. Furthermore, the interface 110 employs file fidelity checks by calculating checksum values for each FCS file and the FCS file's associated artifacts. As examples, these checksums may be SHA or MD5 checksums. After calculating the checksum for each data file, the interface 110 generates a manifest listing each file contained in the ACS file as well as each data file's associated checksum value. This manifest may be an XML manifest or an XML table of contents, but other manifest file types may be employed. The interface 110 may generate a text file (.txt) to store the manifest XML or data. The FCS files within the ACS file may be compressed so that the acquisition computer 104 transmits smaller files to the server 106.

The interface 110 may automatically generate a name for the ACS file when creating the ACS file. For example, the interface 110 may encode a timestamp into the ACS file name. For example, the ACS file may have a file name according to the following format: <year>.<month>.<dayNumber>.<timestamp>.acs.

It should be understood that the ACS container and the Table of Contents are simply examples of containers and associated metadata and instructions.]

The interface 110 may allow a user to select one or more locations as destinations for uploading the ACS file (see, for example, FIG. 13A discussed below). The interface 110 can specify the destination location(s) as a global setting for a particular data type (e.g., if the ACS file contains FCS files then to the interface 110 can specify that the ACS file is to be routed to a particular server such as a FlowJo Enterprise server; as another example, if the ACS file contains sequencing data, the interface 100 can specify that it should be routed to a sequencing analysis server, etc.). The interface can detect the type of data by examining the file extension, data structure. Furthermore, because the interface can query the hardware to which it is connected the interface can also determine the capability of the connected 'service. The interface 110 may upload the ACS files to an analysis computer (e.g., server 106), a central repository, a cloud, a networked computer, or any other location electrically connected to the acquisition computer 104. FIG. 2 illustrates that the ACS container is uploaded to an analysis server 106 that performs data management, data pre-processing, and analysis protocols.

When the analysis server 106 receives the ACS container, the server 106 unpacks the ACS container to find the FCS files contained therein. The server 106 checks the manifest against the FCS files found in the unpacking to verify that the FCS files listed in the manifest match up with the unpacked FCS files. The server 106 further performs a data quality check by calculating the checksums for each data file contained in the ACS container and then compares the calculated checksums with the checksums listed in the manifest to verify that the checksums match up. If any discrepancies exist, the server 106 determines that data was corrupted in transit and requests the interface 110 to resend another ACS container. Referring to FIG. 2, the processes described above are illustrated in the I. Data Management section 220.

When uploading data from the acquisition computer 104, users may also annotate their experiments. Users may add additional metadata which is written to the raw data files themselves through a header or may create a 'workspace' which associates metadata with files. By allowing users to upload other columnar data with their raw data from the instrument, additional metadata can be associated with the raw sample data through sample name, sample location, or a lookup. Finally, users can annotate data at the interface itself by importing this columnar metadata/data or manually annotating the files. Annotation creates an XML file providing metadata about the acquired FCS files, and the annotated metadata is added to the ACS file. The interface 110 may provide a graphical user interface including form boxes where users can enter information that annotates the experiment. As part of the annotation, the interface 110 may require a user to select a manufacturer and a model of the acquisition instrument 102 so that subsequent users may easily find out which instrument 102 was used to acquire the sample data. Annotation may further include describing the sample's source, reagents used during acquisition, date, researcher's name, experiment's purpose, the institution performing the experiment, and other types of experiment identification. Annotation facilitates cataloguing to enable file and result querying, data sharing, and linking to other data types.

The interface 110 may additionally receive data indicating the type of instrument 102. The server 106, in turn, can leverage this information to remotely configure the instrument 102 through the interface 110. That is, the server 106 may analyze data acquired by the instrument 102 and find the data unsatisfactory. For example, if the server 106 determines that the sample data fails to fall within a range of cell frequencies in comparison to a control sample, the server 106 may request that another sample be analyzed by the acquisition instrument 102 or that the instrument configuration be checked or modified. As such, the server 106 may flag the data as not conducive for analysis. Furthermore, the server 106 may suggest using a new reagent or different instrument 102 configurations to generate better data (such as an adjusted voltage of the instrument 102, with adjusted compensation, etc.). If the server 106 requests new samples under different conditions, the interface 110 may interact with the acquisition software 108 to adjust the conditions under which the instrument 102 collects the sample. The interaction between the interface 110 and the acquisition software 108 may be performed using an API that interacts with the acquisition software 108 to adjust the parameters of the instrument 102.

As the instrument 102 collects data, the instrument 102 and the acquisition software 108 generate metadata. The metadata may include reagents used, patient ID, data identifying the instrument 102, and any other type of data. The interface 110 may extract the metadata generated by the instrument 102 and the acquisition software 108 to store the metadata in a database. Plaintext metadata can be extracted from the headers of raw data and marked-up metadata from an acquisition workspace can be extracted using those markups.

In addition, because the interface 110 connects the acquisition computer 104 with the analysis server 106, a user through the interface 110 may review or create new template components that define an automated analysis of the acquired data to be run on the server 106 after acquisition. In other words, a user may cause an analysis of the acquired data to be commenced instantly after that data is acquired from the instrument 102 and transferred to the server 106 or in real-time. By leveraging the metadata of the files generated by the acquisition software 108, the interface 110 can automate analysis of experiments, run quality control analysis of the data acquired by the instrument 102, and facilitate the server's 106 ability to compare data to previously run samples. For example, users can associate a given acquisition 'run' with a study which allows for comparing the results from this run of data to others which are part of that study on the server. Stored metadata may allow a researcher to determine whether or not a sample was analyzed using a particular set of reagents. This cataloguing helps to prevent the same experiments being performed multiple times, and also helps researchers decide which experiments to perform in the future. Learning from the results of experiments helps design better future experiments. Finally, the metadata links the FCS files to any other associated metadata such as a patient's ID, associated files, or any other information.

Because the interface 110 links the acquisition software 108 to the analysis server 106, a data set may be sent to an analysis pipeline on the server so that reports and workspaces are generated immediately upon data transfer, which is described in more detail below. This immediate analysis saves researcher time and provides near-instant results. Also, by immediately transferring the files for analysis, a researcher may receive a notification as to the sample quality while still in the lab and near the instrument 102. Thus, a poor sample may be quickly identified and another sample may be run, perhaps under new instrument conditions and configurations, before the analyst leaves the lab.

FIG. 2 illustrates that the server 106 is configured to perform Pre-processing and Analysis Protocol. These features are described in more detail below. In summary, these features provide automated analysis of the uploaded data. Also, these processes result in batch sample status reports, batch results, raw data, and large detailed analysis reports. Because the interface 110 provides a link between the server 106 and the acquisition computer 104, the analysis server 106 is able to generate outputs, such as workspaces, plots, and reports, more quickly than conventional methods.

Figure 3:
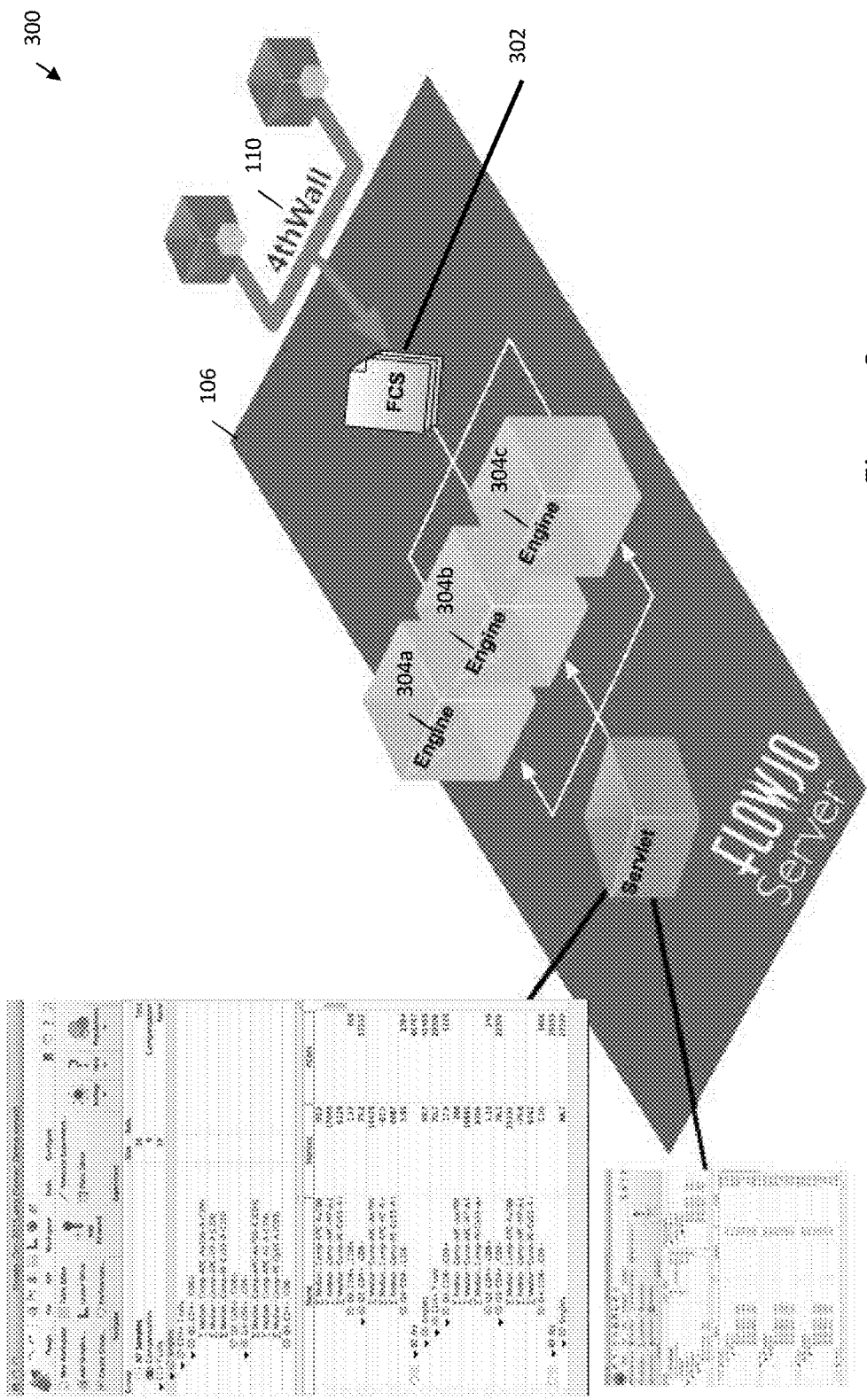
FIG. 3 illustrates an expanded view of the server illustrated in FIG. 2.

FIG. 3 illustrates an example block diagram 300 that shows how the interface 110 provides sample data to the server 106 for analysis. As shown in FIG. 3, through the interface 110 (labeled as $4^{th}$ Wall in FIG. 3), the server 106 receives one or more FCS files 302 after unpacking an ACS file. The FCS files 302 are fed to analysis engines 304*a*, 304*b*, 304*c* running on the server 106. Through, for example, an application or web client, a user may create and save execution protocols to analyze the data contained in the unpacked FCS files 302. Users can load and manipulate server-based data files in a workspace as if the data were stored on a local computer.

FIG. 3 illustrates as an example three analysis computing engines 304*a*, 304*b*, 304*c*. These engines 304*a*, 304*b*, 304*c* may process analysis templates in parallel. The engines 304*a*, 304*b*, 304*c* may be arranged in a parallel and/or pipelined arrangement such that the engines may analyze the data simultaneously. In a pipelined arrangement, the output of one engine 304*a*, 304*b*, 304*c* may be the input of a second. The engines 304*a*, 304*b*, 304*c* may perform parallel processing using a template or pipelined processing using workspace files.

Figure 13A:
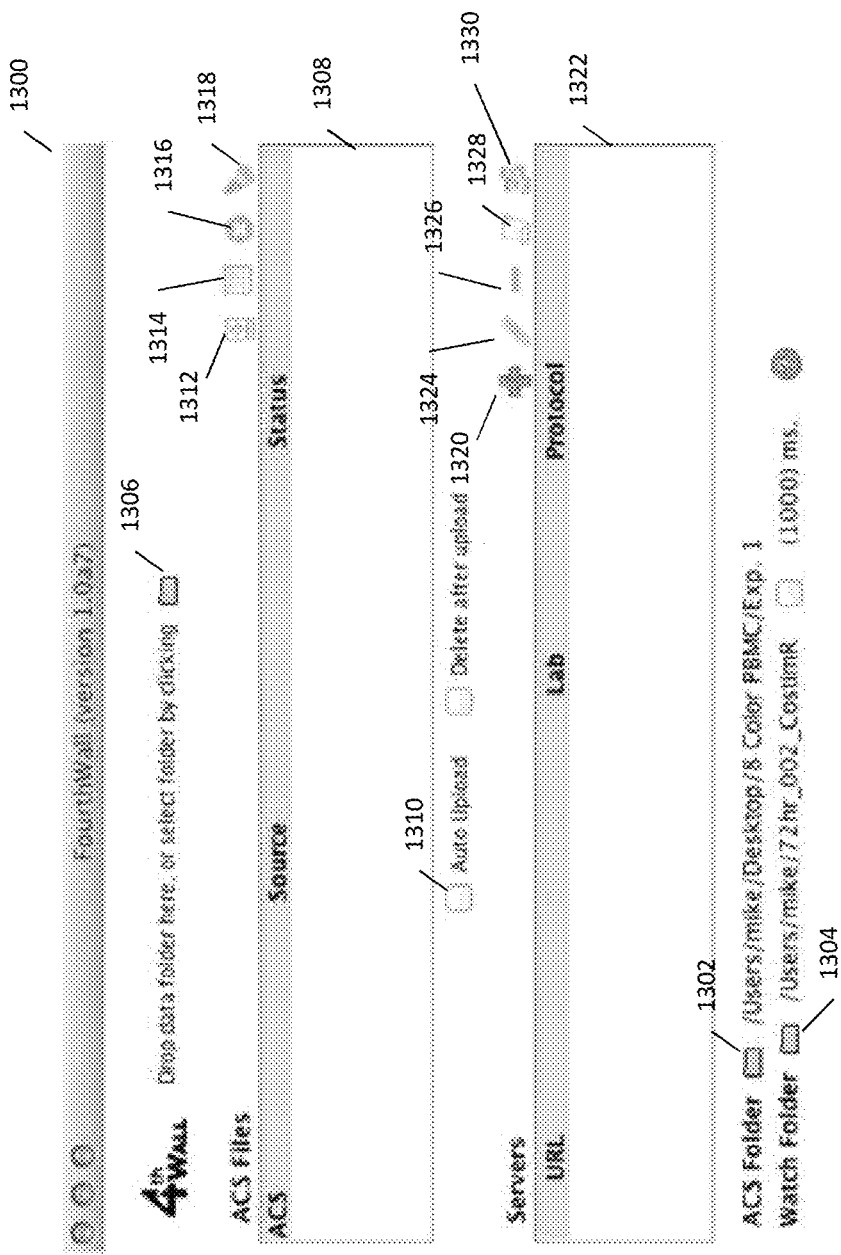
FIGS. 13A and B illustrate exemplary graphical user interfaces (GUIs) for interacting with and configuring the interface.

Referring now to FIG. 13A, FIG. 13A illustrates an exemplary graphical user interface (GUI) 1300 for interacting with and configuring the interface 110. Within the GUI 1300, a user can select an ACS folder and a watch folder. For example, when the user first interacts with the GUI 1300, the GUI 1300 may prompt the user to select the ACS folder and the watch folder. The ACS folder is a file directory location where the interface 110 will store generated ACS files it creates as well as a log file that tracks and logs all uploaded ACS files. The watch folder is a file directory location where FCS files generated by the acquisition software 108 are saved and where the interface 110, in an example embodiment, will look for a predetermined file that indicates that the contents of the folder are ready to be collected and uploaded by the interface 110. For example, the predetermined file may be a file named Manifest.txt, wherein Manifest.txt is the manifest data file described above that lists all the FCS files created by the acquisition software 108, however other file types and file names may indicate that the files generated by the acquisition instrument 102 are ready to be uploaded to the server 106. The user may select the ACS folder by selecting an ACS folder selection icon 1302, and the user may select the watch folder by selecting a watch folder selection icon 1304. Upon selection of these icons, the user will be prompted to enter or identify the folders that are to serve as the ACS folder and the watch folder.

In the exemplary GUI 1300 illustrated in FIG. 13A, the ACS folder has already been selected as /Users/mike/Desktop/8 Color PBMC/Exp. 1, and the watch folder has already been selected as /Users/mike/72hr_002_COstimR. The interface 110 may periodically check the watch folder for the predetermined file, and the user may configure how often the interface 110 checks the watch folder. In the exemplary GUI 1300 illustrated in FIG. 13A, the interface 110 has been set to check the watch folder ever 1000 ms.

When the interface 110 (operating in an automated data push mode) detects the predetermined file in the watch folder, the interface 110 copies the entire contents of the watch folder to the ACS folder. Within the ACS folder, the interface 110 will create a uniquely named sub-folder, which may include a timestamp. After copying the files to the sub-folder, the entire contents of the sub-folder, including the manifest, are compressed into an ACS file and uploaded to a selected server 106.

While the interface 110 is configured to check the watch folder, the GUI 1300 also allows a user to select a previously created ACS file or a set of FCS files (and associated artifacts and metadata) from an experiment to upload. In such a user-triggered mode for the interface 110, a user may either select the files through a file manager by selecting a find data files icon 1306 or by dragging and dropping files or a folder into an ACS files box 1308.

The interface 110 may be configured to automatically upload files selected or dragged into the ACS files box 1308 by selecting an Auto Upload check box 1310. When the Auto Upload checkbox 1310 is selected, ACS files are automatically uploaded to a selected server 106. When the Auto Upload checkbox is not selected, the user may upload ACS files by selecting an upload icon 1312.

Also associated with the ACS files box 1308 is a see table of contents icon 1314 that is configured to display a table of contents for a selected ACS file. The table of contents may list all the FCS files associated with the ACS files as well as any checksum values for the files. Further, the GUI 1300 comprises a delete file icon 1316 that is configured to delete a selected ACS file and a delete all files icon 1318 that deletes all ACS files shown in the ACS files box 1308.

Figure 13B:
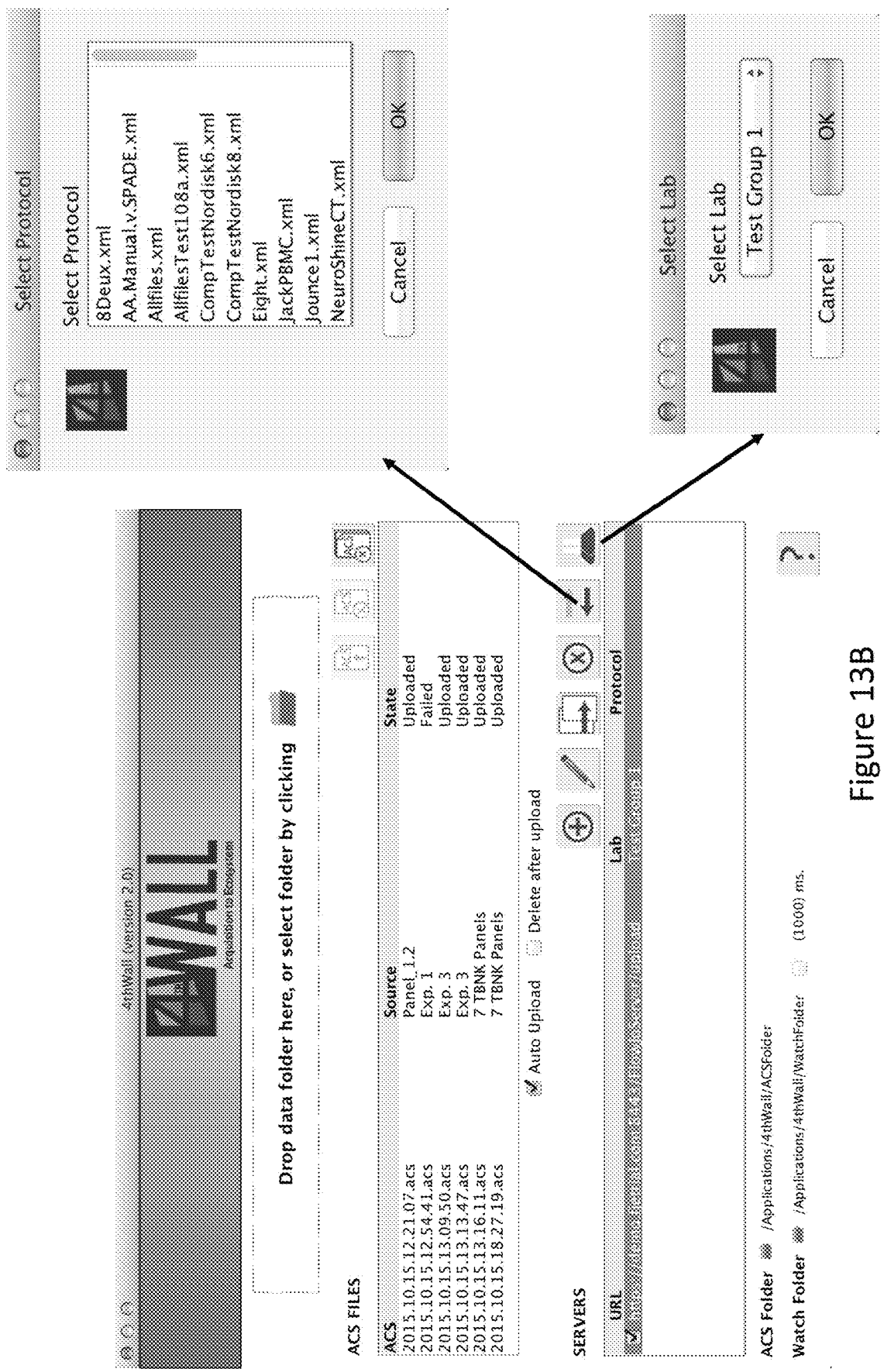

The user can select one or more server 106 locations to upload the ACS files by selecting an add server button 1320. The add server button 1320 opens a dialogue to enter a URL for a server 106. Once a URL for a server 106 has been entered through the dialogue, the server 106 appears in a server list 1322. Also associated with the server list 1322 is an edit server URL icon 1324, a remove server icon 1326, a specify protocol icon 1328, and a specify lab icon 1330. The edit server URL icon 1324 is configured to open a dialogue that allows the user to re-enter a URL for a selected server 106. The remove server icon 1326 is configured to remove an added server 106 from the server list 1322. The specify protocol icon 1328 is configured to open a selection menu to specify an analysis protocol to execute on the ACS file after the ACS file has been uploaded to an analysis server 106. FIG. 13B shows an example GUI which shows how a user can specify a protocol that is to be run on the data. FIG. 13B further shows how a user may specify a lab to be associated with the uploaded ACS file. The number and types of analysis protocols may depend on the selected server 106, as not every server 106 may include every analysis protocol. Accordingly, the choices presented by the GUI of FIG. 13B as to protocols may be selected as a function of the specified lab. The list of labs available for selection via the GUI can be restricted to only those labs for which the user has upload authorization based on the acquisition computer's 104 hardware address.

The interface 110 may authorize itself with a selected server 106 using the acquisition computer's 104 hardware address (e.g. MAC address). The analysis server 106 may authorize the interface 110 when the interface 110 has a recognized hardware address, and the hardware address may be registered with the analysis server 106 for authentication purposes. The interface 110 may communicate with the analysis server 106 using a secure connection, such as by using a secure sockets layer (SSL) handshake. The initial connection with the analysis server 106 may be through a non-secure URL. When connecting through the non-secure URL, the server 106 may return to the interface 110 whether the interaction requires a public certificate to encrypt further communication. If so, the interface 110 may automatically download the certificate into an installation folder, and subsequently switch to a secure URL at the direction of the analysis server 106.

FIG. 14 illustrates a method 1400 for uploading scientific data to a remote server. The method 1400 begins when the instrument 102 acquires data while analyzing a scientific sample in step 1402. The instrument generates signals that are interpreted by the acquisition software 108, and the acquisition software 108 converts the signals generated by the instrument into data files, such as FCS files in step 1404. After all the FCS files are created, the interface 110 detects the presence of a full set of FCS files for an experiment in step 1406. The interface 110 may detect the presence of a full set of FCS files by monitoring a watch folder and looking for a manifest file, or by determining that no temporary files exist in the watch folder. In another embodiment, a user may indicate the location of a full set of FCS files to the interface 110 through a GUI, such as the GUI 1300.

After finding a full set of FCS files for an experiment, the interface 110 creates a container data file containing all the FCS files, associated experiment artifacts and metadata, a manifest, and checksum values in step 1408. The container data file may be, for example, an ACS file. In addition, the container data file may comprise compressed versions of the FCS files.

Subsequent to creating the container data file, the interface 110 initiates and establishes a secure connection with the server 104 in step 1410. Establishing and initiating a secure connection with the server 106 may comprise pinging a non-secure URL, providing authentication credentials or authenticated hardware addresses, and receiving access to a secure URL. After establishing the secure connection, the interface 110 uploads the data container data file to the server 106 over the secure connection in step 1412. The interface 110 may further provide commands indicating how to perform analysis of the scientific data uploaded to the server 104. For example, the interface 110 may command the server 104 to user a specific protocol template saved on the server 106 for analysis of the uploaded scientific data.

Accordingly, it can be seen that the inventive interface design provides a mechanism for efficiently moving lab data from a scientific instrument to a remote server for analysis.

Additional, the inventive interface design provides for improved data provenance because the interface and its interaction with the scientific instrument/acquisition computer and server provides a full chain of custody from sample to raw data and eventually to produced report. Moreover, the interface 110 provides assurance that data is backed up and may be deleted, which limits data duplication and allows regular or continuous cleanup of the acquisition computer which typically has a limited disk and is undesirable for serving as a location for long-term data storage and archiving.

Further still, the inventive interface design provides data quality control (QC) across multiple touch points. Through the data quality checks described herein, the interface and server are able to avoid data loss or corruption in the transfer. Moreover, as another QC example, as data may be sent to the server or streamed to the server, analysis may be performed to examine the quality of the fluorescence/event-level data itself (e.g., by examining the slope of medians of fluoresce versus time) or recognize events like carry-over between samples, clogs of the instrument, or flow-rate inconsistencies—all signatures that may be detected, flagged, and corrected if applicable during an ongoing acquisition run. The interface and its interaction with the server provide an ability to use constraints (i.e. decision criteria) in protocols, as discussed below, which can be used to ensure that the samples to be collected compare to a control, and fall within a certain expected range. This check can allow a greenlighting of the current acquisition run, e.g. by checking that a control with a known cell frequency falls within certain bounds.

Modular Experiment Templates

An experiment template includes components that define an entire analysis, excluding the actual data files (such as FCS files). The experiment template may include all the parameters for organizing and analyzing sample data. Modular experiment templates break a full experiment template down into individual steps or operations via modular experiment template components. Each modular experiment template component may be configured to organize data representing the samples so that decisions can be made at the end of each experiment step. The modular nature of the experiment templates breaks apart the signal processing, analysis, reporting, etc. steps of an entire sample experiment into individual components so that the components may be used in combination to define an entire analysis. In addition to defining an entire experiment analysis, the modular template components may be shared between experiments and analysts. By piecing together a string of modular template components (using a protocol pipeline, described below), an analysts can quickly and easily define an entire experiment analysis having desired characteristics. Also, by making the template components reusable, the time to create an entire experiment template is minimized.

Using the modular experiment template approach, each modular experiment template component embodies an experiment analysis step or operation (e.g. organizing data, gating, analysis, reporting). In this way, a template component is an object representing one or more analysis algorithms that effect calculation, sample organization, or reporting. These individual steps may include gating, compensation, clustering singlets (removing sample data indicating connected cells passing through flow cytometer), sample quality control, generating a report, live-dead cell stain, organizing populations, applying gating trees, creating graphs, adding additional metadata to sample data, or any other algorithm performed. A modular experiment template component may have other non-experiment-related functions as well, such as updating a database with the results of the analysis, sending an email to another user with the results, and updating a catalogue indicating that the experiment under these conditions and parameters has been run. A template component may specify its algorithm or operation in a file such as an XML file.

Because the template is broken down into individual components, these modular experiment templates are repeatable. In this way, even if a reagent is changed, most of the same modular experiment templates may be reused in subsequent experiments. For example, if one reagent is changed from a first set of samples to a second set, most of the same modular template components may be re-used, as many of the same analysis conditions (which gates to apply, when to report, when to apply compensation, etc.) will be applied to a new set of samples such as the same gating techniques. Also, some modular template component algorithms are applied to just about every sample such as quality control analysis, compensation, and singlets analysis. Additionally, the modular template components are additive such that more analysis components may be added to an existing set of modular template components.

Because of their modular nature, the product of a previous analysis step may become the input of another. For example, to begin an analysis, the interface 110 above may submit some data representing a plurality of samples to the server 106. The server 106 may receive the data and execute one or more modular templates on the received data. The server 106 may first apply a first modular template component that corresponds to a gating tree that finds peripheral blood mononuclear cell (PBMC) populations within the data. After applying that gating tree, the server 106 may apply a second modular template component that analyzes the PBMC populations and creates a group that contains only samples whose PBMC populations are below a certain threshold. In this way, the first modular template component generates a number representing the number of cells in the PBMC population, which may be represented by a percentage of the PBMC cells out of the total number of cells in the sample. Then, the second modular template component receives the PBMC population numbers (e.g. percentage numbers) generated by the first modular template component to determine which samples have PBMC populations below a given threshold (e.g., a threshold percentage). In other words, these modular template components constrain the amount of data processed by the next template. By constraining the data, only data of interest is analyzed, and the amount of processing performed by the server 106 is reduced relative to conventional systems, which frees processing resources for other tasks and thus improves throughput so that experimental results can be produced and delivered faster than conventional methods.

Figure 4:
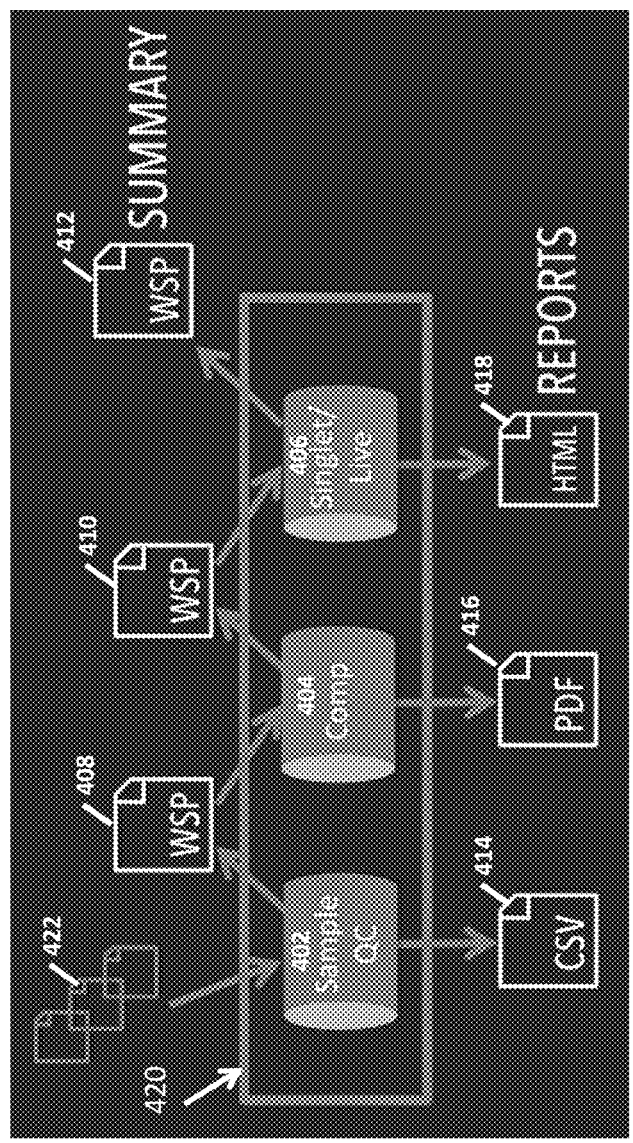
FIG. 4 illustrates an example protocol pipeline comprised of a plurality of modular experiment templates.

FIG. 4 illustrates three template components 402, 404, 406 packaged together in a pipeline 420 (discussed below): a sample quality control template component 402, a compensation template component 404, and a singlet/live cell template component 406. Each modular component 402, 404, 406 generates a workspace data object 408, 410, 412 and artifacts 414, 416, 418 for analysis. The objects and artifacts/derivatives can be stored on the server and are associated with the raw data by file URI's. These objects/artifacts can remain stored on the server until archived or moved to another server. Furthermore, each workspace and its associated derivatives can be versioned and a database internally keeps track of each revision, which will receive a new version number.

Figure 5:
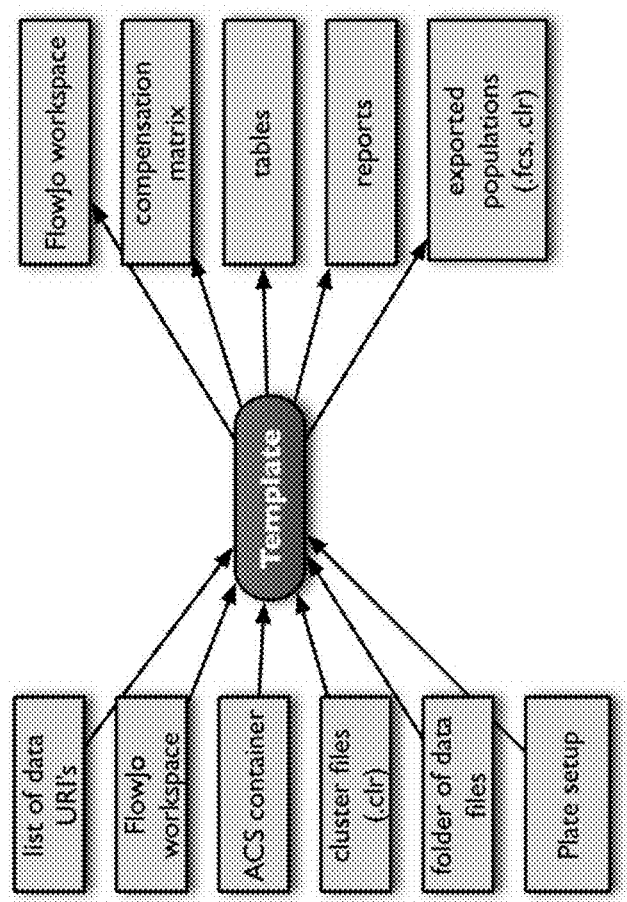
FIG. 5 illustrates the file types that may be used as inputs for a template component.

The first template component (sample QC) 402 receives data files 422 representing samples acquired from an instrument 102. These files 422 may be in the form of FCS data files, a list of data file uniform resource identifiers (URI), an ACS container, CSV files, PDF files, CLR files, workspace files understood by analysis software (such as FlowJo), cluster files, metadata, or various other types of files representing sample data. FIG. 5 illustrates the types of files that a template component 402, 404, 406 may receive and the types of files a template component 402, 404, 406 may output.

Most notable from the list above is the ability for a template component 402, 404, 406 to receive analysis software workspace files because each template component 402, 404, 406 generates a new workspace data file or amends an existing workspace file. As shown in FIG. 4, each template component 402, 404, 406 generates a workspace data file (WSP) 408, 410, 412, and the workspace data file 408, 410, 412 output by a previous template component 402, 404, 406 becomes the input of a subsequent template component 402, 404, 406. In this way, template components 402, 404, 406 are additive. FIG. 4 illustrates only three template components 402, 404, 406, but the "Summary" workspace file 412 output by the singlets/live template component could become the input for a fourth library template component simply by adding another template component to the pipeline. Because the "summary" workspace file 412 contains the results of the sample QC template component 402, the compensation template component 404, and the singlets/live template component 406, a processor performing the experiment analysis does not need to re-execute the first three template components 402, 404, 406 if a researcher decides to add one or more additional template components to the experiment analysis. The fourth template component needs to only find the workspace file 412 created by the third template component 406 shown in FIG. 4. In this way, template components can be used as part of a protocol to build hierarchical analysis conditionally, flag samples, and create reports.

In addition to creating workspace files 408, 410, 412 used by analysis software, the template components 402, 404, 406 may also create artifacts 414, 416, 418 that can present analysis results to applications outside of the analysis software 108. These artifacts 414, 416, 418 and workspace data objects 408, 410, 412 provide the results of each component's 402, 404, 406 analysis, algorithm, or command. Thus, a researcher may see data results generated by each component 402, 404, 406. FIG. 4 illustrates that the Sample QC template component 402 may generate a CSV artifact 414, the compensation template component 414 may generate a PDF artifact 416, and the singlet/live template component 406 may generate an HTML-based artifact 418. However, it should be understood that these file format for artifacts are examples only, and each template component may generate artifacts 414, 416, 418 using other file formats if desired by a practitioner. Also, it should be understood that not every template component 402, 404, 406 generates a workspace 408, 410, 412 and an artifact 414, 416, 418, as some may only generate workspace files or only generate artifacts.

Because of the modular nature of the template components 402, 404, 406, template components 402, 404, 406 may be easily modified. Parameters, actions, and algorithms are easy to change in either a command-line or GUI based format to change, revise, or extend analysis of a template component 402, 404, 406. Also, as template components 402, 404, 406 are created and built, researchers can build libraries of template components thereby allowing for template components 402, 404, 406 to be reused in other experiment analysis and shared with other researchers also connected to the analysis server 106. The analysis server 106 may store all the created template components 402, 404, 406 in a database to compile a library of template components. So, for example, once a researcher creates a gating tree or a sample organization template component, that template component may be used in any other data set by any other researcher in any other experiment.

Figure 15:
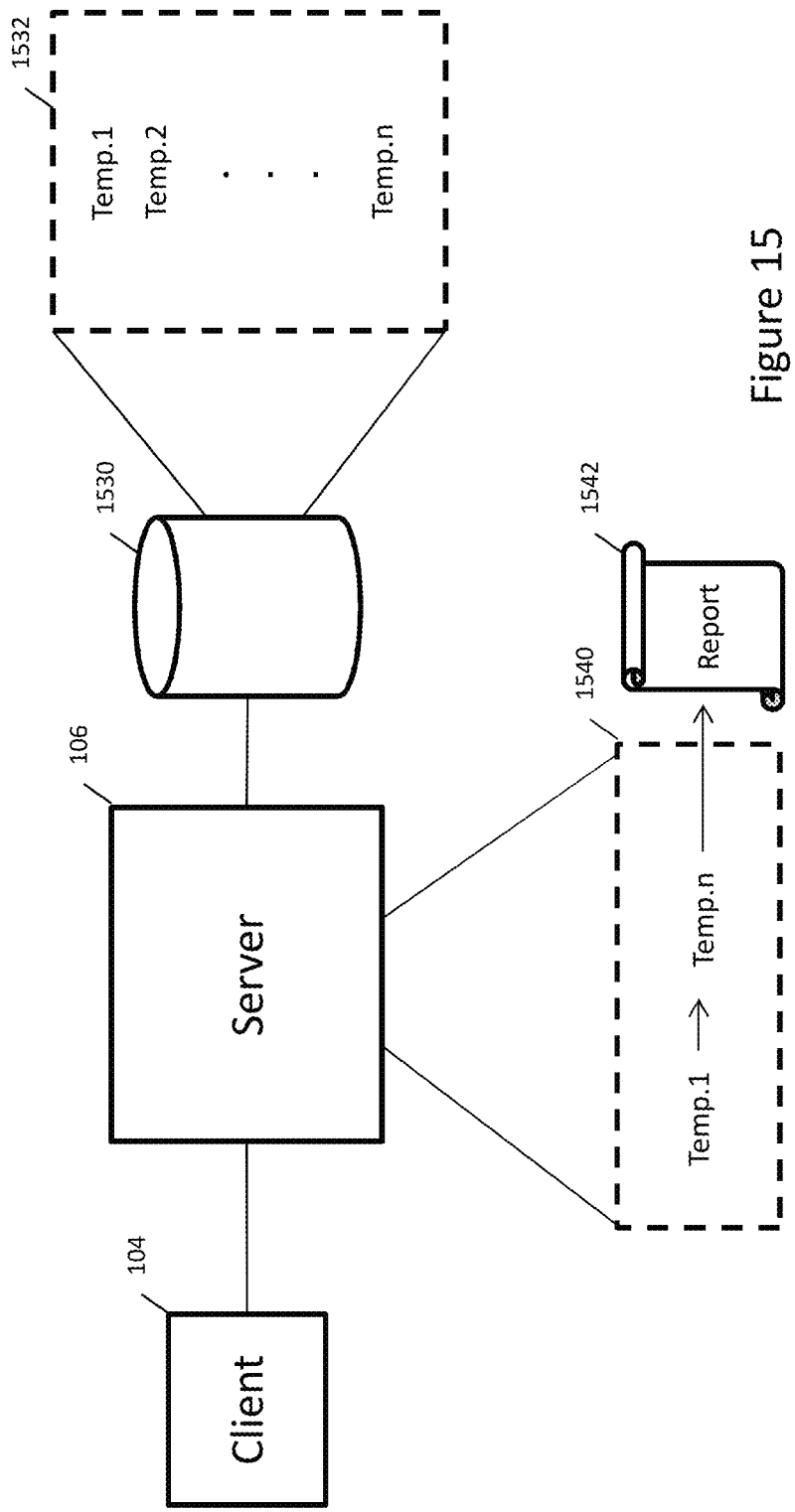
FIG. 15 illustrates how a server may store a library of template components in a database for reuse.

FIG. 15 illustrates how a server may store a library of template components in a database for reuse. A client computer 104, such as the acquisition computer 104, communicates with a server 106 over a network. The server 106 is electronically connected to a database 1532. The database 1530 is configured to store modular template components created by users. The database 1530 creates a library 1532 of modular template components, which can be selected by users to be used in an experiment analysis. A user of the client computer 104 may create additional template components and save the newly created template components in the library 1532.

When a user selects one or more template components from the library 1532, the server 106 creates a protocol 1540, which may be in the form of a pipeline. The protocol performs analysis on scientific experiment data provided by the client computer 104 based on the selected or created template components. In the protocol 1540 illustrated in FIG. 15, the protocol 1532 comprises two template components: Temp.1 and Temp.n. The protocol 1540 results in a report 1542 that summarizes the analysis of the protocol 1540.

Template components may be configured to perform numerous operations. The following list is not exhaustive of all the operations a template component could perform. The template components may perform hierarchical analysis (i.e. a binding node), repeated analysis steps, third-party population identification, population identification statistical comparison, population name-mapping, scripted analysis, reporting, adding metadata, and interfacing with external library information management systems (LIMS) or databases. Each of these will be described in more detail below.

Figure 6:
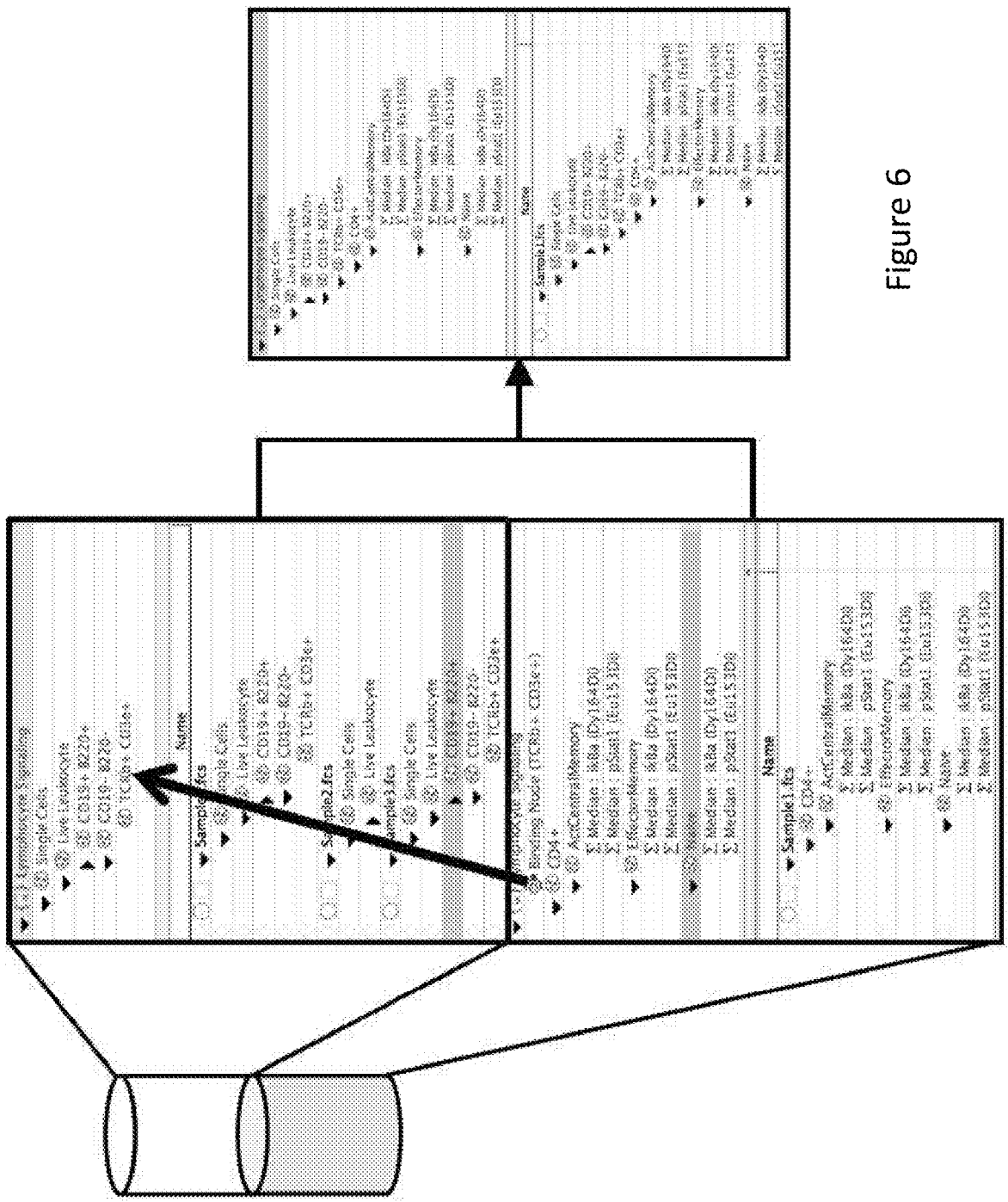
FIG. 6 illustrates a binding node created in a graphical user interface (GUI).

Regarding hierarchical analysis, a binding node preserves the hierarchical analysis of data (see U.S. Pat. No. 6,178, 382). In this way, hierarchical gates may be applied in modular fashion. Importantly, the name of the binding point is also a naming criterion that must be satisfied when the library template is executed. For example, FIG. 6 illustrates how one gating tree binds to the "TCRb+CD3e+" in the workspace GUI and applies the gates and statistics at that level of the hierarchy, to a group of samples.

Figure 7:
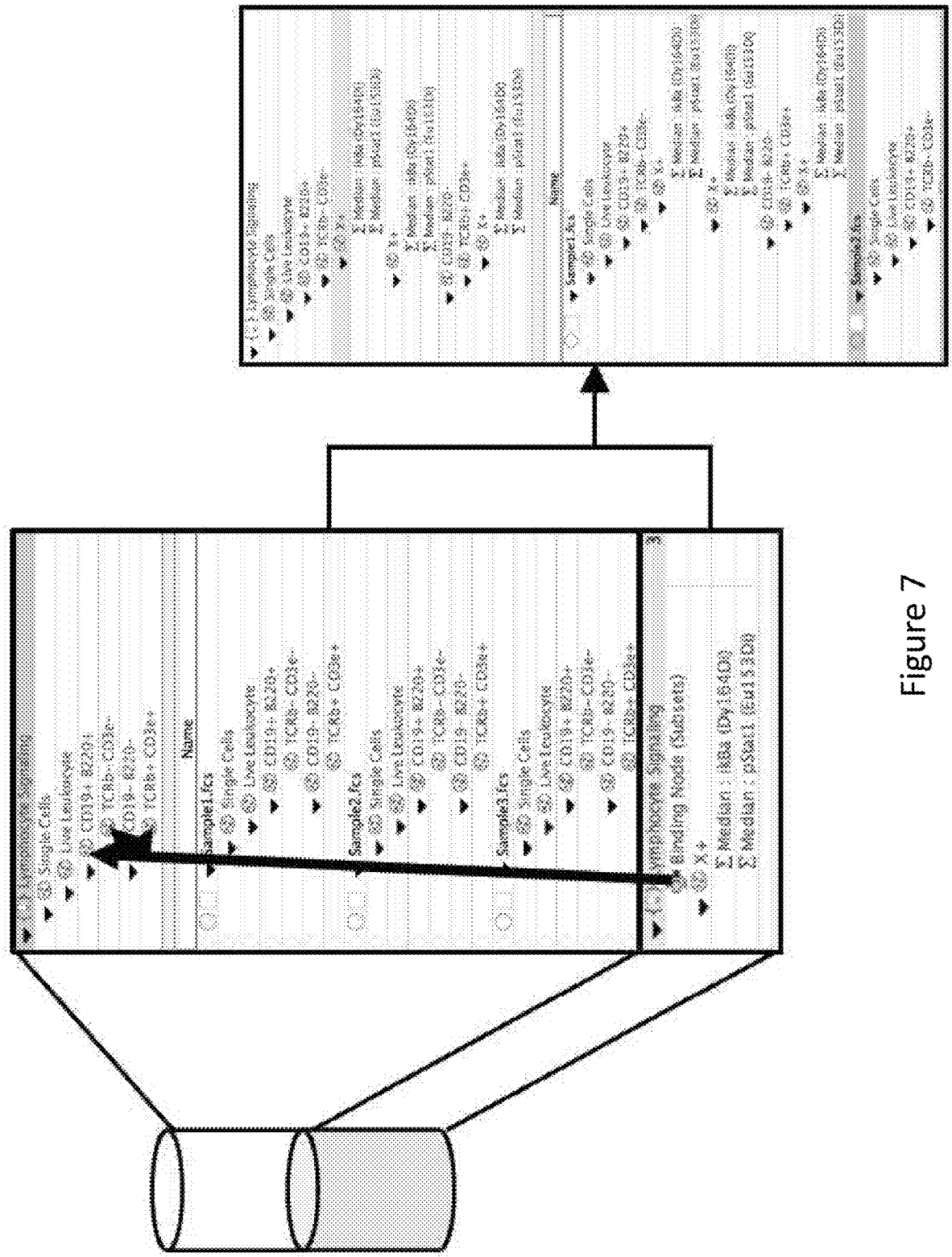
FIG. 7 illustrates repeated analysis created in a GUI.

Regarding repeated analysis, the modularity of a template component means that repeated analysis steps may be created once and applied via binding nodes. Binding Nodes allow the addition of new gates to a previously existing population within a gating tree. Thus, FIGS. 6 and 7 show that the logic of binding nodes allows an analysis (in this case, a set of gates and statistics) to be applied to a particular subset of data from a sample. Thus, a module of analysis may be applied to a subset of the raw data, and this allows for the building of complex hierarchical analysis. For example, the binding node may be applied to many samples at the same time through group application, and that the binding node serves as a physical structure that abstracts a target subset of data to which its child analyses will be applied. As another example, FIG. 7 illustrates a gate on X+ events and 2 statistics on that subpopulation may be bound to several subsets at once.

Figure 8:
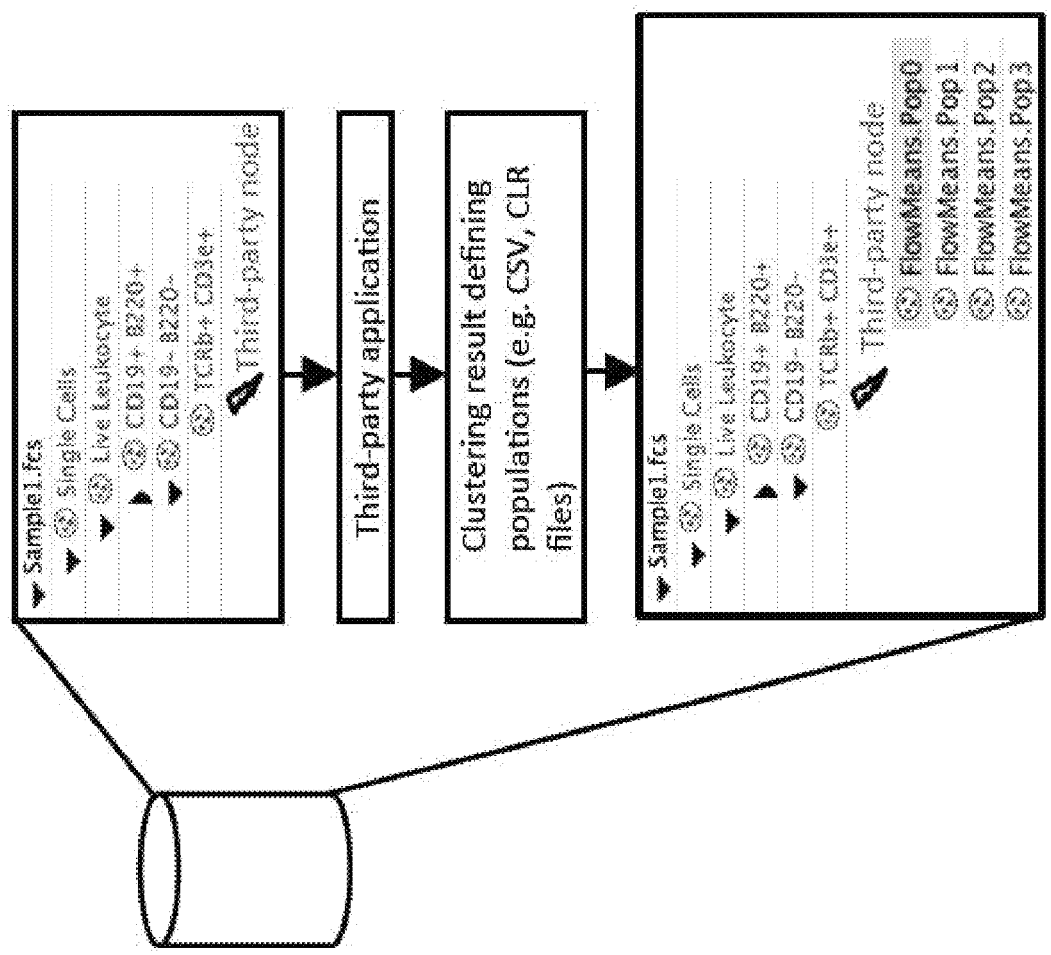
FIG. 8 illustrates a third party population identification operation invoked in a GUI.

Regarding third-party population identification, templates components may call out to third-party applications (e.g. the statistical program R) on the fly, pass these applications subpopulation event-level data for population identification through clustering and import the artifacts produced by these third-party applications (which define inclusion, exclusion, or probability of inclusion into a population, currently supported as a CSV or CLR file) into the analysis software so that they may be treated as new populations and new derived parameters. This makes the population identification by any clustering algorithm automatable, applicable to groups, and seamless with the analysis performed by the analysis software. Also, any downstream analysis may be applied to these new subpopulations. FIG. 8, illustrates how third party applications may be invoked through a binding node.

Figure 9:
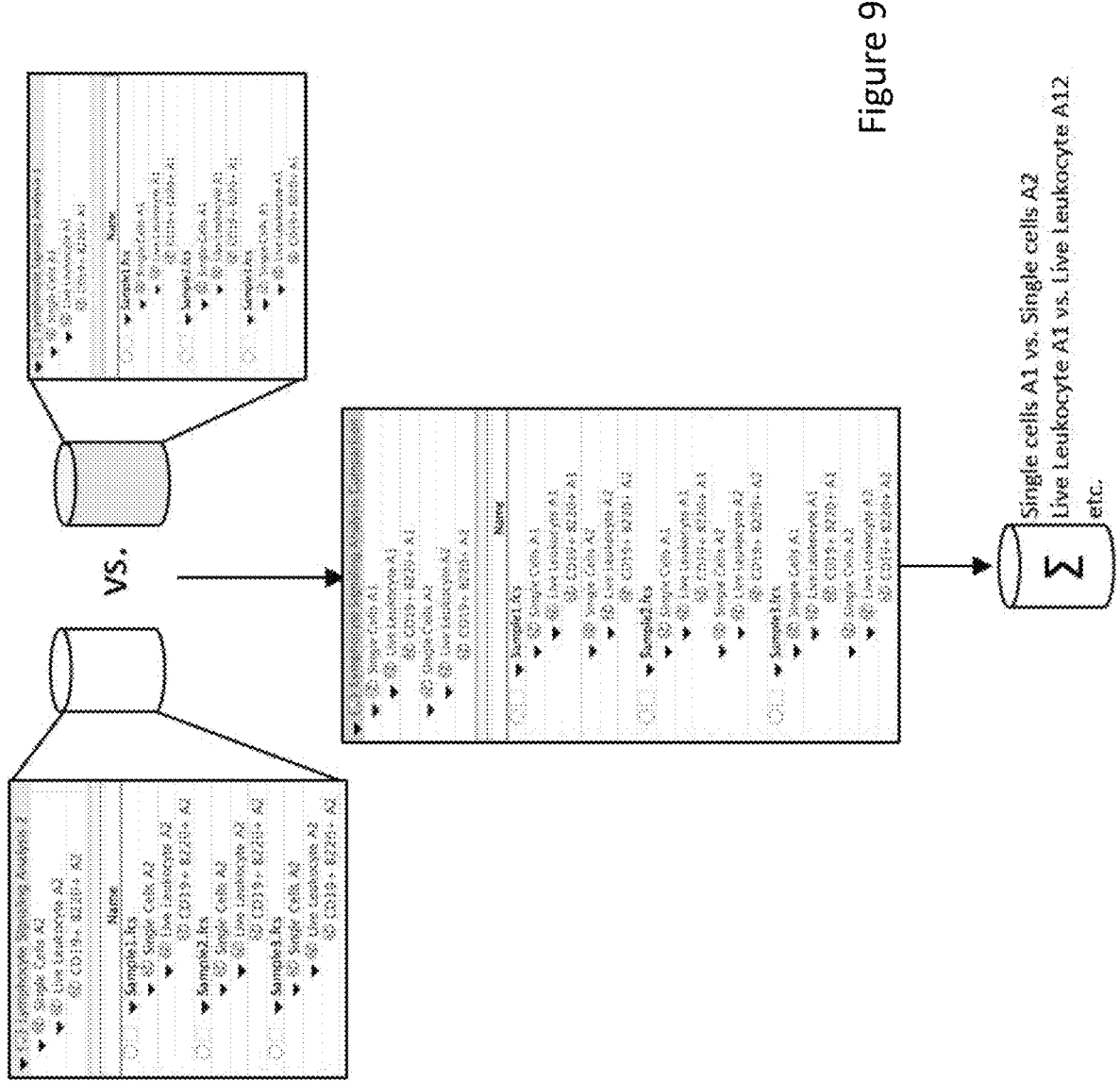
FIG. 9 illustrates a population identification statistical evaluation operation invoked in a GUI

Regarding population identification statistical comparison, any number of population identification algorithms may be compared using a template component. In this manner, more than one manual or automated analysis may be combined into one workspace artifact and thus compared using the following statistical comparisons (e.g. Single Cells A1 from analyst 1 vs. Single Cells A2 from analyst 2). Cytometry-specific statistical evaluations, which normalize control and test histograms to the same area, subtract them and determine a positive percentage, exist such as SED and Overton subtraction as well as the statistical tests Chi-Square, and F-Measure, the latter which is a standard statistical test in the field for comparing gate inclusion/exclusion. FIG. 9 illustrates two samples populations may be compared statistically in an analysis software GUI.

Figure 10:
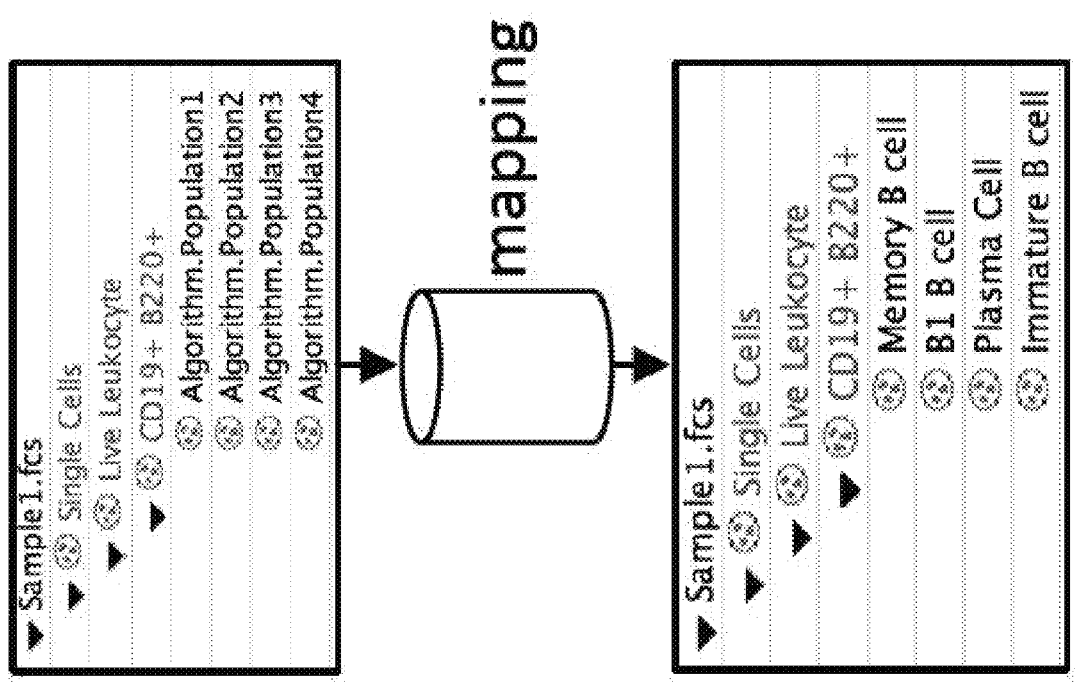
FIG. 10 illustrates a population name mapping operation invoked in a GUI.

Regarding population name-mapping, following the automated discovery of populations/clusters as described above, it is important that these clusters be mapped to human-understandable names. There are three options for doing this mapping, statistical mapping, cluster mapping, and de novo naming. For statistical mapping, the similarity of populations is compared using the aforementioned statistics and user thresholds are set for the degree of like-ness that must be met for populations to be considered the same. For cluster mapping, the similarity of clusters/populations may be compared in n-dimensional space and mapped to previously defined and named populations. And, for de novo naming, for populations that lack a population name, users may set their default preferences for new population naming. For example, a first algorithm may name a population by mapping to a particular (known or unknown) cell phenotype (e.g. "CD4 Regulatory T cells" for CD3+CD4+CD25+Foxp3+ cells), a set of marker expression levels (e.g. "CD44midCD62LhiCD4+CD3+"), or a list of defined population names. FIG. 10 illustrates how a library template may provide name mapping to data within the sample data.

Regarding scripted analysis, a library template may perform, for example, a mathematical function, enhanced sample organization, flagging, dynamic sample analysis, or extensible implementation. For a mathematical function, any mathematical functions may be performed on analysis within a template component: e.g. CD4:CD8 ratio for examining HIV progression. For enhanced sample organization, samples may be included into groups based on statistics or metadata/keywords which may be created as an analysis is executed, which may allow for the subsetting of "hits" in a study or the generation of reports specific for flagged samples. For flagging, a script may execute on conditional criteria e.g. statistics above a certain threshold leading to metadata flagging or metadata/keyword derivation from statistics or groups, such that samples receive additional keywords and annotation. For dynamic sample analysis, a gate defining a population may be drawn based on statistics, such that populations are defined dynamically (can change based on the ongoing analysis). Finally, for extensible implementation, any functionality using the analysis software—gates, statistics, metadata keywords, samples, and groups may be created on a customizable basis e.g. metadata can be used to set gates for individual subsets in an index-sorted experiment (where individual cells are divided into individual wells).

Finally regarding reporting, any tabular or graphical reports may be created and used as part of a template component. Thus, common reports can be modularized and added to analysis pipelines. In addition, the plugin architecture allows a template component to establish a link to a LIMS, repository, or database to use any of the data and elements as input, update a specified table, put artifacts in a specified location, or use naming or metadata elements from these data stores. This also allows for the extension of visualization tools and importing those artifacts into a workspace, the possibility to integrate with open and save functionalities for communicating with other services' API's (e.g. LIMS, database, etc.), and exporting of populations, statistic tables, or chart objects for any other type of 3rd-party application.

Protocol Pipelines

As described above, the modular template components are individual components which may be used together to generate results of an experiment. Protocol pipelines combine a plurality of modular template components together to generate a processing pipeline that represents an entire experiment analysis. Referring to FIG. 4, the box surrounding the three template components represents the protocol pipeline.

As a first layer, the protocol pipelines define the ordered execution of the modular template components. For example, a first template component may apply gating to gather all the PBMCs, a second template component may find all samples having a low amount of PBMCs (e.g. less than 55%), and a third template component may generate a batch report of the samples having a low amount of PBMCs. A protocol pipeline may tie these three template components together to present an ordered execution.

However, protocol pipelines are not necessarily a linear order of a plurality of template components. That is, between template components, constraints may be applied. The processor uses one or more constraints to determine whether to execute a subsequent template component and/or which subsequent template component to execute. In some situations, multiple constraints may need to be satisfied before the processor executes a subsequent template component. For example, a protocol pipeline may only execute a second template component if the results of the first template component satisfy a condition. Or, alternatively, the protocol pipeline may execute a third template component if the results of a first template component don't satisfy a condition. These constraints generate a decision tree depending on how the constraint is structured. A constraint may reference groups, gates, and statistics to determine whether a condition is satisfied. Users can define constraints for a protocol pipeline based on what they want to set as criteria based on their knowledge of biology and previous studies.

By using the results of a template protocol algorithm as the input of a subsequent template protocol algorithm, a protocol pipeline may constrain the amount of data presented in a report summarizing the entire analysis generated by a protocol pipeline. The protocol pipeline thereby focuses an analyst's attention on the most meaningful information for the analysis. Also, the processor performs less processing down the line because less data is processed at the end of the pipeline. Using again the PBMC example above, the processor only generates reports about samples having a low PBMC count. For example, perhaps seven samples were provided to the processor and two samples had low PBMC counts. Thus, the processor would only need to generate reports about two of the seven samples. Because of this data constraint, the processor performs less processing, the results are generated more quickly by the processor, and the analyst only reviews reports about samples of interest.

A protocol pipeline as represented by a file or other data structure specifies the conditional execution of one or more template components, as defined above. Based on the satisfaction of constraints, which are decision points in the execution, the protocol pipeline (1) specifies a pipeline of templates or template components to be executed, (2) executes subsequent templates or template components if constraints are satisfied, and (3) provides the results of a previous template or template component as an input to a subsequent template or template component. The protocol pipeline can build pipelines of templates and template components, such as a pipeline to apply hierarchical gating, report generation, database updating, etc., which can be used in future studies.

A full protocol pipeline may manage the execution of the template components to generate a full execution pipeline, which may include data pre-processing (i.e. signal vs. time quality analysis, or comparing sample results to a known control sample), algorithm-based analysis, report creation, and linking results with a LIMS or database.

Also, in combination with the interface 110 described in the first section, the protocol pipelines allows for the execution of analysis directly from the acquisition instrument 102. Therefore, the protocol pipeline can execute its analysis, generate results, reports, and workspaces immediately upon data transfer to the analysis server 106 from the acquisition instrument 102.

Figure 11:
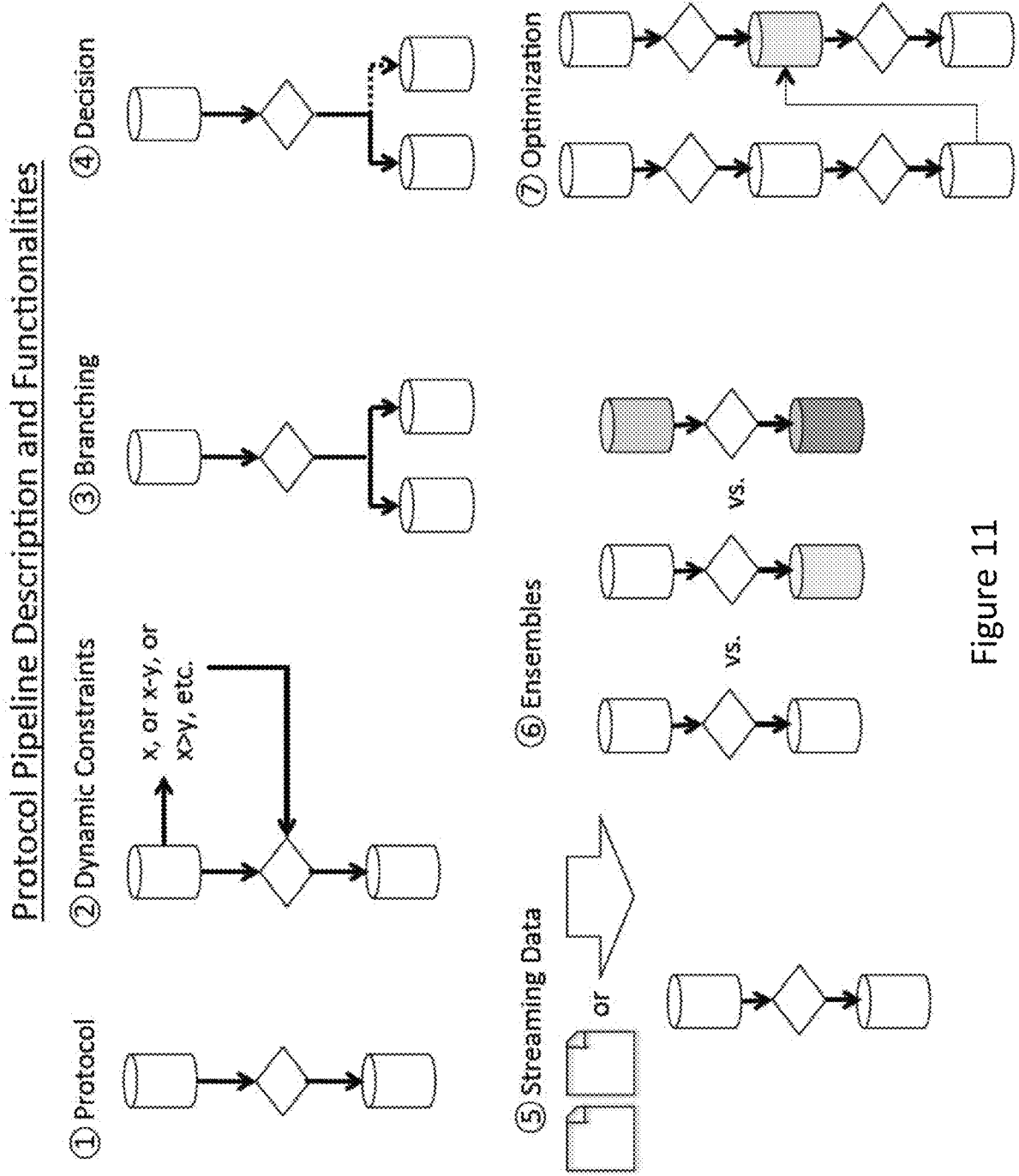
FIG. 11 illustrates potential protocol pipeline paths and functionalities.

FIG. 11 illustrate potential protocol pipelines created using different types of constraints. These pipelines may include a protocol, dynamic constraints, branching, decision trees, streaming data, ensembles, or optimization.

A protocol specifies the conditional execution of library template components, based on the satisfaction of constraints, which are decision points in execution. For the descriptions and functionalities described below, it is important to note that (1) a template object comprises a specification of one or more analysis algorithms, an algorithm that performs a calculation, sample organization, or reporting; and (2) a constraint is a specification of a decision point between the execution of analysis steps which may either be set ahead of time (static) or dynamic in that a constraint may change as the results of the current or concurrent analyses are determined or may change based on the analysis that has occurred in another protocol.

Dynamic Constraints:

A constraint may change based on the results of an ongoing analysis in the same protocol (or indeed another protocol which has been executed previously or concurrently), which indicate variables for the decision criterion of a constraint (x, one variable; x-y, a range; or x>y, etc.).

Branching:

Protocols may branch, such that a constraint dictates different paths, e.g. use of library template(s)) of analysis of different subsets of data.

Decision:

In a branched protocol, a constraint may dictate a decision to use a given path of analysis (use of library template(s)) based on the results of an ongoing analysis.

Streaming Data:

A protocol may be used on static data (e.g. .fcs files exported and saved from an acquisition instrument 102) or on streaming data.

Ensembles:

A meta-protocol may run several protocols to determine the best analysis strategy, where one or more components in a protocol pipeline may be different but accomplish an analogous task, and a determination of the best pipeline made using the automated application of population-identification statistics.

Optimization:

Closely related to the use of ensembles, an iterated, automated fashion, a protocol can validate their own analysis as described above and identify weak points which can be optimized. In this manner, the protocol can exchange its components e.g. to better identify clusters of cells using different algorithms.

Selection & Prediction:

A protocol, using metadata (e.g. labeled parameters which indicate staining panel and thus possible routes for population identification—CD3, CD4, and CD8→CD3+, CD3+CD4+, CD3+CD8+ populations) or user-defined variables (e.g. "identify CD4+ T cells") can determine which library template to use in an analysis to identify appropriate populations, generate relevant reports, and use correct plug-in mechanisms (e.g. to update the correct table in a database). Auto-protocol or "predictive pipelining," wherein all the parameters in all the files are examined, the analysis server 106 determines if there is an existing set of library templates that would apply, a protocol is constructed on the fly, and executed automatically.

Adaptive Analysis A:

In the first type of adaptive analysis, a protocol changes based on the ongoing analysis. The results of an ongoing analysis help determine the next step of analysis, rather than the library template being pre-determined. This would occur by a user selecting a possible set of library templates, or having the analysis server 106 scan the available library templates, and the protocol selecting the next set of analysis algorithms based on these results.

Adaptive Analysis B:

In an extension of A, above, the results of a protocol may indicate that previous analyses need to be updated. In this case, the analysis that is executed on one set of files (1) may be applied in toto to other files or previous workspace artifacts which already contain an analysis; (2) a protocol which is related to one previously applied to a set of data is updated and applied on the fly to similar data sets or previously generated workspace artifacts; or (3) additional analyses (algorithms, reports, etc.) are added to an existing analysis using a protocol.

As described above, a protocol pipeline can be represented by an XML file specifying constraints for a hierarchical execution. An example protocol XML file comprises <Protocol> elements, where each element specifies a template to be executed. The template to be executed is specified as the value of the 'templateName" attribute. In an example embodiment, no file path information is necessary to specify the template; the server 106 can manage the storage of template files. The following example illustrates a protocol to execute a single template:

<Protocol templateName="Antilge.wspt'/>

When this template is executed, the analysis results can be saved in a workspace file that is managed by server 106.

To create a pipeline of template execution, <Protocol> elements are nested in the protocol XML file. The nesting of <Protocol> elements determines the order of execution, where the output of one execution (a workspace file) is used as input to the next. The server 106 can provide the initial input of a folder of data files to the top level <Protocol>. In the following example, a folder of data files is input to the Antilge template, a sample quality report is generated, and the analysis results are written to a workspace file. Next, the analysis of the TCellStats template is merged with the workspace, a report is generated showing a graph of all populations in the merged workspace, and the workspace is written with the new, combined analysis.

```
<Protocol templateName='Antilge.wspt' options="-sampleQuality"/>
    <Protocol templateName="TCellStats.wspt' options="-allGraphs"/>
</Protocol>
```

It is possible for a <Protocol> element to have one or multiple <Protocol> child elements, and each one is executed in order. In the following example, three templates are executed in order after the initial Antilge template.

```
<Protocol templateName='Antilge.wspt'/>
    <Protocol templateName="TCellStats.wspt'/>
    <Protocol templateName="THelperPopulations.wspt'/>
    <Protocol templateName="CTLPopulations.wspt'/>
</Protocol>
```

The protocol XML file may also specify constraints via <Constraint> elements. A <Constraint> element can define a numerical condition that must be true for all members of a group in the workspace. To define a constraint, a user can specify a group, a population that exists in that group, a statistic (and optionally the parameter on which that statistic is calculated), and an evaluation formula. The following example illustrates the attributes that are used to specify a constraint according to an example embodiment of a protocol XML file.

```
<Constraint groupName="Panel1" population="Lymphocytes"
    statistic="fj.stat.freqofparent" eval=">.50"/>
```

In this example, the constraint is evaluated for all samples in the group named 'Panel1'. For each of these samples, the gating tree is searched for a population named 'Lymphocytes'. If no population by that name is found, the constraint is not satisfied. For each population that is found, a search is conducted for the "Freq. of Parent" statistic, and if not found, the constraint is not satisfied. Finally, for each statistic, the value of the statistic is evaluated for the expression '>0.50', i.e., is greater than 50%. If all lymph populations for each sample in the Panel1 group are more than 50% of their parent populations, then the constraint is satisfied.

Another example illustrates a constraint where the statistic is calculated on a specific parameter.

```
<Constraint groupName="Panel1" population="TCells"
    statistic="Median" parameter="APC- AX700-A" eval=">10000"/>
```

To evaluate a constraint on the count of a population, it is not necessary to explicitly create a Count statistic as a child of the population since the count is already stored for each gated population in the workspace. To specify a constraint on the root sample, a user can omit the 'population' attribute, or specify an empty population, i.e. population="". The following example constraint is only satisfied if all samples in the workspace have more than 1000 events.
<Constraint groupName="All Samples" population=""statistic="Count" eval=">1000"/>

It is also possible to specify a constraint based on the number of samples in a group. This increases the power of constraint evaluation since group inclusion criteria can be based on keyword values. The following example shows how to require that a group named 'Compensation' (the compensation controls) has at least 8 samples.

<Constraint groupName="Compensation" statistic="groupCount" eval=">=8"/>

Constraints are evaluated prior to the execution of a protocol, and it is possible to specify multiple constraints in a protocol XML file. A template specified by a protocol XML file is executed only if all of its constraints are satisfied. The constraints for a specified template are specified as children in the XML hierarchy. In the example below, the protocol for template 2 is executed only if both constraints for the group 'abc' and 'xyz' are satisfied. Additional, the protocol for template 3 is executed only if constraints for group 'efg' are satisfied.

```
<Protocol templateName="1">
    <Protocol templateName="2">
        <Constraint groupName="abc" .../>
        <Constraint groupName="xyz" .../>
        <Protocol templateName="3">
            <Constraint groupName="efg" .../>
        </Protocol>
    </Protocol>
</Protocol>
```

Accordingly, it can be seen the use of nested protocols and constraints in a protocol data structure such as an XML file makes it possible for a user to build complex conditional execution of template gating strategies to generate reusable and robust analysis. FIG. 12 illustrates another example XML file of a protocol pipeline. The protocol specified by FIG. 12 calls multiple templates and also applies multiple constraints to determine how the execution will continue.

The following example shows how template components and protocol pipelines can be implemented to achieve an entire experiment analysis by breaking the analysis steps into modular template components combined using protocols and constraints. In this example, neuroendocrine modulation of immune function clinical data is described. The clinical data may have 120 gates and statistics of interests for each sample over twelve time-points. The goal of the experiment analysis may be to (1) calculate compensation, after setting a custom gate size for a live/dead (AARD) compensation control, (2) flag samples by generating reports during analysis if the dead cell frequency is >30%, (3) not analyze CD4/CD8 ratio if the T cell subset is <100 events, (4) generate a sample quality report, (5) generate charts of any samples that have a dead cell frequency >30%, and (6) generate the ratio of CD4:CD8 T cells, heat mapped.

To accomplish goals 1-6, a user may select or create the following templates:

First, a user may create an empty template where data is to be loaded. This template is also configured to generate a sample quality report. This template performs the necessary pre-processing on the scientific data.

Second, a user creates a second template that creates a group to an AARD sample. This template applies a large gate to the AARD sample data that includes enough positive events to calculate a compensation matrix. This template may also create a second group with all "Run" samples by searching for file names having the word "run" in the same name. Finding the "Run" samples and grouping them facilitates the grouping of samples to which analysis will be applied after compensation is applied and calculated. The compensation matrix command may be applied to the Run Samples Group using a compensation command within the protocol created later.

Third, the user creates or selects a time, singlets, and live gating template component. The time gate uses a SSC-A v.

Time graph to exclude, for example, the first 1000 events to limit carry over. The Singlets gate uses a FSC-H v. FSC-A graph and draws the gate along the y=x line. Also, the love gate uses SSC v. AARD graph using a polygon on negative.

Fourth the user creates a template component samples where the dead cell frequency is >30% by entering a script to include only samples which contain a high percentage of dead cells.

Fifth, the user creates or loads a template component configured to flag samples where the dead cell frequency is greater than 30%. This template may be configured to generate a report for all samples that get flagged using a report editor, such as the FlowJo Enterprise Layout Editor.

Sixth, the user creates or loads a template component configured to set additional gates on the "Live" population gate set by the third template component. These gates are bound to the Live gate, and the gates set by the sixth template component 1) set a large PBMC gate to exclude debris according to the SSC-A v. FSC-A graph, set a quadrant gate which subsets B and T cells according to a CD3 v. CD19 graph, set a statistic to determine the frequency of live cells that are B cells, and finally set a gate that subsets CD3+ T cells into CD4 and CD8 subsets according to the CD4 v. CD8 graph.

Seventh, the user creates or loads a template component configured to ignore any samples where the CD4/CD8 ratio is <100 events. This template component may comprise a script that filters samples having a CD4/CD8 ratio >100 events. This template may further generate reports and heatmaps for the non-filtered samples.

Figure 16:
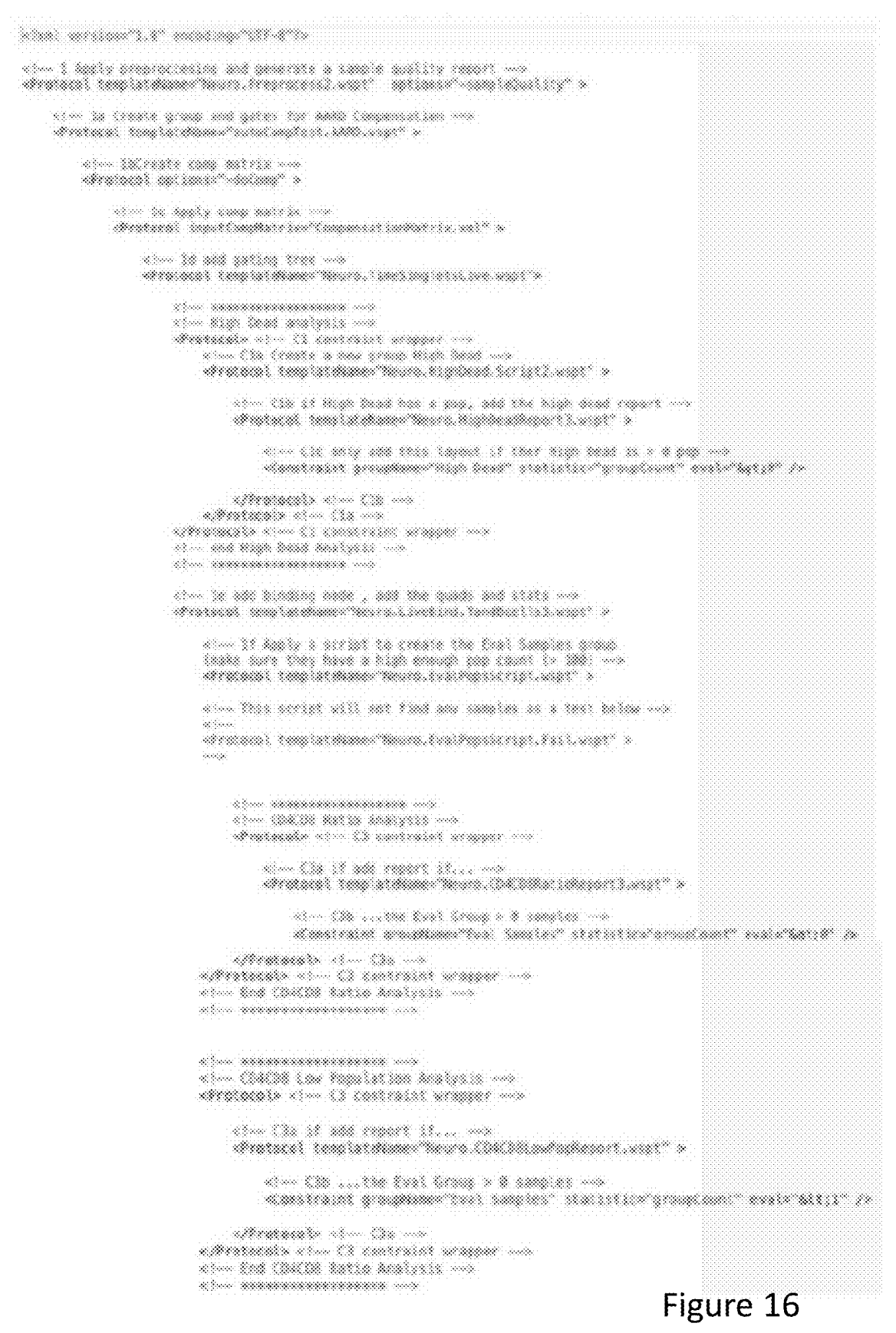

Finally, a user combines all 7 template components into a protocol pipeline including applying constraints. The protocol may be written in a tagged format such as XML or combined using a GUI that automatically creates the XML file. An example XML protocol is illustrated in FIG. 16. A template component is called whenever the <protocol TEMPLATE NAME> command is invoked, and a constraint is applied anytime the <constraint> command is called.

In view of the foregoing, it will be seen that the several advantages of the invention are achieved and attained.

The embodiments were chosen and described in order to explain the principles of the invention and its practical application to thereby enable others skilled in the art to utilize the invention in various embodiments and with various modifications as are suited to the particular use contemplated.

What is claimed is:

1. A method for integrating a scientific instrument with a remote computer system, the method comprising
    receiving scientific data related to a biological sample from a scientific instrument;
    creating a container data file, wherein the container data file comprises one or more scientific data files representing the received scientific data and a manifest data file listing the one or more scientific data files contained within the container data file;
    establishing a network connection with a remote computer system;
    transmitting the container data file to the remote computer system over the network connection;
    receiving a command over the network connection from the remote computer system to acquire new scientific data under different acquisition parameters in response to an analysis by the remote computer system of the scientific data within the transmitted container data file;
    controlling the scientific instrument in accordance with the received command to cause the scientific instrument to acquire the new scientific data using the different acquisition parameters;
    transmitting, to the remote computer system over the network connection, the new scientific data; and
    transmitting, to the remote computer system over the network connection, a protocol command causing the remote computer system to perform an analysis on the new scientific data, wherein the protocol command identifies a protocol template associated with the analysis to be performed by the remote computer system and wherein the protocol template is stored by the remote computer system, wherein the method is performed by a processor.

2. The method of claim 1 wherein the scientific instrument is a flow cytometer.

3. The method of claim 1 wherein the processor performs the method steps during an ongoing acquisition run such that the controlling step comprises the processor controlling the scientific instrument as it acquires the new scientific data.

4. The method of claim 3 wherein the processor performs the transmitting step in real-time as the scientific data is generated by the scientific instrument to stream the scientific data over the network connection to the remote computer system for the analysis.

5. The method of claim 1 wherein the remote computer system comprises an analysis server configured to analyze the scientific data contained within the container file.

6. The method of claim 5 further comprising:
    the analysis server performing the analysis specified by the protocol command on the scientific data within the transmitted container data file; and
    in response to the analysis, the analysis server sending the command for acquiring new scientific data under different acquisition parameters to the processor over the network connection.

7. The method of claim 1 further comprising the processor compressing the scientific data files before creating the container data file, and wherein the container data file comprises compressed versions of the scientific data files.

8. The method of claim 7 wherein the container data file further comprises metadata indicating parameters and conditions of the scientific instrument while the scientific instrument acquired the scientific data.

9. The method of claim 8, wherein the metadata further indicates at least one member of the group consisting of scientific instrument type, patient identification data, a reagent used during data acquisition, user-submitted annotations, and a digital signature.

10. The method of claim 1 further comprising the processor calculating checksum values for each scientific data file contained within the container data file, and wherein the manifest data file lists the calculated checksum values associated with each scientific data file.

11. The method of claim 1 wherein the connection is a secure connection, and wherein the establishing step comprises the processor:
    pinging the remote computer system through an unsecure uniform resource locator (URL);
    exchanging authentication credentials with the remote computer system to gain access to a secured URL; and
    switching to the secure URL at the direction of the remote computer system when the remote computer system authorizes the processor based on the exchanged credentials.

12. The method of claim 11, wherein the authentication credentials comprise a MAC address associated with the processor.

13. The method of claim 11, further comprising the processor monitoring a watch folder file directory where the scientific data files are stored; and
- detecting a predetermined data file indicating that the scientific instrument has finished acquiring scientific data; and
- creating the container data file and establishing the secure connection after the processor detects the predetermined data file.

14. The method of claim 13, wherein the processor automatically creates the container data file and uploads the container data file upon detection of the predetermined data file.

15. The method of claim 14 wherein the predetermined data file comprises the manifest data file.

16. The method of claim 1 wherein the analysis by the remote computer system indicates that the scientific data contained in the scientific data files is unsatisfactory.

17. The method of claim 1 further comprising:
- the processor generating a graphical user interface configured to accept a selection of a modular template component specifying a portion of an experiment to be performed as part of the analysis, wherein the analysis comprises a plurality of modular template components, at least one of the plurality of modular template components being shared between the experiment and at least one other experiment; and
- the processor receiving the selection of the modular template component and sending the selection with the container data file thereby causing the remote computer system to conduct the analysis on the scientific data contained in the container data file in accordance with the modular template component associated with the selection.

18. The method of claim 1 wherein the container data file is an archival cytometry standard (ACS) file.

19. The method of claim 1 wherein the processor is resident on a member of the group consisting of (1) an acquisition computer associated with the scientific instrument, and (2) the scientific instrument.

20. The method of claim 1 wherein the command comprises an instruction for using a new reagent to acquire the new scientific data.

21. The method of claim 1 wherein the command comprises an instruction for using a different instrument configuration for the scientific instrument to acquire the new scientific data.

22. The method of claim 21 wherein the different instrument configuration comprises at least one of an adjusted voltage of the scientific instrument and an adjusted compensation of the scientific instrument.

23. The method of claim 1 wherein the protocol template includes a constraint, and wherein the scientific data includes at least one value associated with the constraint.

24. The method of claim 1, further comprising creating a new container data file, wherein the new container data file comprises one or more new scientific data files representing the new scientific data, wherein the new scientific data are transmitted to the remote computer system over the network connection via the new container data file.

25. A computer program product for integrating a scientific instrument with a remote computer system, the computer program product comprising:
- a plurality of processor-executable instructions that are resident on a non-transitory computer-readable storage medium, wherein the instructions are configured for execution by at least one processor to cause a computer to at least:
- receive scientific data related to a biological sample from a scientific instrument,
- create a container data file, wherein the container data file comprises one or more scientific data files representing the received scientific data and a manifest data file listing the one or more scientific data files contained within the container data file,
- establish a network connection with a remote computer system,
- transmit the container data file to the remote computer system over the network connection,
- receive a command over the network connection from the remote computer system to acquire new scientific data under different acquisition parameters in response to an analysis by the remote computer system of the scientific data within the transmitted container data file,
- control the scientific instrument in accordance with the received command to cause the scientific instrument to acquire the new scientific data using the different acquisition parameters,
- transmit, to the remote computer system over the network connection, the new scientific data, and
- transmit, to the remote computer system over the network connection, a protocol command causing the remote computer system to perform an analysis on the new scientific data, wherein the protocol command identifies a protocol template associated with the analysis to be performed by the remote computer system and wherein the protocol template is stored by the remote computer system, wherein the method is performed by a processor.

26. An apparatus for integrating a scientific instrument with a remote computer system, the apparatus comprising:
- a processor configured to execute an interface, the interface configured to bi-directionally link a scientific instrument with a remote server to (1) transfer scientific data acquired by the scientific instrument over a network connection to the remote server, and (2) transfer operational data for controlling an operation of the scientific instrument from the remote server over the network connection to the scientific instrument,
- wherein the interface is further configured to provide a protocol command over the network connection to the remote server to cause the remove server to perform an analysis on the scientific data transferred to the remote server, wherein the protocol command identifies a protocol template associated with the analysis to be performed by the remote server and wherein the protocol template is stored by the remote server.

27. The apparatus of claim 26 wherein the transferred operational data comprises a command from the remote server to acquire new scientific data under different acquisition parameters in response to an analysis by the remote server of the transferred scientific data; and
- wherein the interface is further configured to control the scientific instrument in accordance with the command to cause the scientific instrument to acquire the new scientific data using the different acquisition parameters.

28. The apparatus of claim 27 wherein the interface is further configured to transfer the scientific data to the remote server in real-time during an acquisition run by the scientific instrument.

29. The apparatus of claim 28 wherein the interface is further configured to (1) receive the command from the remote server during the acquisition run and (2) control the scientific instrument in accordance with the received command to cause the scientific instrument to acquire the new scientific data using the different acquisition parameters during the acquisition run as it is ongoing.

* * * * *